United States Patent
Kim et al.

(10) Patent No.: US 8,784,752 B2
(45) Date of Patent: Jul. 22, 2014

(54) USE OF CHEMICALLY PATTERNED SUBSTRATE FOR LIQUID HANDLING, CHEMICAL AND BIOLOGICAL REACTIONS

(75) Inventors: Namyong Kim, Palo Alto, CA (US); Kong Leong Cheng, Singapore (SG); Li Li, Singapore (SG); Teow Soon Seah, Singapore (SG)

(73) Assignee: Curiox Biosystems Pte Ltd (SG)

( * ) Notice: Subject to any disclaimer, the term of this patent is extended or adjusted under 35 U.S.C. 154(b) by 0 days.

(21) Appl. No.: 13/264,913

(22) PCT Filed: Apr. 16, 2010

(86) PCT No.: PCT/SG2010/000153
§ 371 (c)(1),
(2), (4) Date: Oct. 17, 2011

(87) PCT Pub. No.: WO2010/120249
PCT Pub. Date: Oct. 21, 2010

(65) Prior Publication Data
US 2012/0035063 A1     Feb. 9, 2012

Related U.S. Application Data

(60) Provisional application No. 61/170,201, filed on Apr. 17, 2009.

(51) Int. Cl.
| | | |
|---|---|---|
| *B01L 3/00* | (2006.01) | |
| *G01N 31/16* | (2006.01) | |
| *B01L 3/14* | (2006.01) | |
| *F04B 19/00* | (2006.01) | |
| *B08B 3/00* | (2006.01) | |
| *C40B 30/00* | (2006.01) | |
| *C40B 60/12* | (2006.01) | |
| *C12M 3/00* | (2006.01) | |
| *C12M 1/34* | (2006.01) | |

(52) U.S. Cl.
USPC ........... 422/551; 422/560; 422/568; 422/503; 422/504; 134/56 R; 506/7; 506/39; 435/288.3

(58) Field of Classification Search
USPC .......................................................... 422/561
See application file for complete search history.

(56) References Cited

U.S. PATENT DOCUMENTS

| | | |
|---|---|---|
| 3,754,872 A | 8/1973 | Zauft |
| 5,219,528 A | 6/1993 | Clark |

(Continued)

FOREIGN PATENT DOCUMENTS

| | | |
|---|---|---|
| DE | 10043042 C2 | 6/2002 |
| EP | 0 812 693 A1 | 12/1997 |

(Continued)

OTHER PUBLICATIONS

Perfluorodecalin-FluoroMed, http://fluoromed.com/products/perfluorodecalin.html (no date).*

(Continued)

*Primary Examiner* — Jill Warden
*Assistant Examiner* — Julie Tavares
(74) *Attorney, Agent, or Firm* — Morgan, Lewis & Bockius LLP

(57) ABSTRACT

Methods and devices for adding liquids to and washing a microfluidic element array are disclosed. The method and devices feature a microfluidic plate holder with a sloped wall for improved draining of liquid, a machine readable/writable identifier, plate leveling systems, liquid filling systems, a hydrophilic-liquid coating, and an automated washing station.

32 Claims, 17 Drawing Sheets

(56) References Cited

U.S. PATENT DOCUMENTS

| | | | |
|---|---|---|---|
| 5,506,121 | A | 4/1996 | Skerra et al. |
| 5,560,811 | A | 10/1996 | Briggs et al. |
| 6,048,908 | A | 4/2000 | Kitagawa |
| 6,086,825 | A | 7/2000 | Sundberg et al. |
| 6,103,493 | A | 8/2000 | Skerra et al. |
| 6,130,098 | A | 10/2000 | Handique et al. |
| 6,238,626 | B1 | 5/2001 | Higuchi et al. |
| 6,331,441 | B1 | 12/2001 | Balch et al. |
| 6,565,813 | B1 * | 5/2003 | Garyantes .................. 422/553 |
| 6,578,952 | B1 | 6/2003 | Sugiyama et al. |
| 6,664,044 | B1 * | 12/2003 | Sato .......................... 435/6.12 |
| 6,716,629 | B2 | 4/2004 | Hess et al. |
| 7,163,823 | B2 | 1/2007 | Patno et al. |
| 7,344,877 | B1 | 3/2008 | Camacho et al. |
| 2002/0094533 | A1 * | 7/2002 | Hess et al. ..................... 435/6 |
| 2003/0083474 | A1 | 5/2003 | Schmidt |
| 2003/0113813 | A1 | 6/2003 | Heidaran et al. |
| 2003/0209560 | A1 | 11/2003 | Hui et al. |
| 2004/0106191 | A1 | 6/2004 | Muser |
| 2004/0136876 | A1 | 7/2004 | Fouillet et al. |
| 2004/0208792 | A1 | 10/2004 | Linton et al. |
| 2004/0234966 | A1 | 11/2004 | Bryning et al. |
| 2005/0045539 | A1 | 3/2005 | Yu et al. |
| 2005/0079105 | A1 | 4/2005 | Hunter et al. |
| 2006/0013031 | A1 | 1/2006 | Ravkin et al. |
| 2006/0051249 | A1 | 3/2006 | Knebel et al. |
| 2006/0105453 | A1 | 5/2006 | Brenan et al. |
| 2007/0003448 | A1 | 1/2007 | Kanigan et al. |
| 2008/0003671 | A1 | 1/2008 | Martin |
| 2010/0000304 | A1 | 1/2010 | Kim et al. |

FOREIGN PATENT DOCUMENTS

| | | | |
|---|---|---|---|
| EP | 1348533 | B1 | 7/2002 |
| EP | 1316360 | B1 | 6/2003 |
| EP | 1 358 939 | A2 | 11/2003 |
| EP | 1 473 079 | | 3/2004 |
| EP | 1 386 657 | | 4/2006 |
| EP | 1 683 571 | | 7/2006 |
| EP | 1 788 047 | | 5/2007 |
| GB | 1 291 610 | A | 10/1972 |
| GB | 2332273 | A | 6/1999 |
| GB | 2334954 | A | 9/1999 |
| JP | 3120453 | | 12/1998 |
| JP | 2002/502955 | | 1/2002 |
| JP | 2003-033177 | A | 2/2003 |
| JP | 2004-020280 | A | 1/2004 |
| JP | 2004-077476 | A | 3/2004 |
| JP | 2004-535176 | | 11/2004 |
| JP | 2005-003803 | | 1/2005 |
| JP | 2005-099004 | A | 4/2005 |
| WO | WO 96/23879 | | 8/1996 |
| WO | WO 98/47003 | | 10/1998 |
| WO | WO 98/55852 | A1 | 12/1998 |
| WO | WO 99/39829 | | 8/1999 |
| WO | WO 99/55826 | | 11/1999 |
| WO | WO 00/14311 | A1 | 3/2000 |
| WO | WO 00/58735 | A2 | 10/2000 |
| WO | WO 01/04144 | | 1/2001 |
| WO | WO 03/029462 | | 4/2003 |
| WO | WO 2004/030820 | | 4/2004 |
| WO | WO 2004/111610 | | 11/2004 |
| WO | WO 2005/019254 | | 3/2005 |
| WO | WO 2005/019255 | | 3/2005 |
| WO | WO 2005/019256 | | 3/2005 |
| WO | WO 2006/004739 | A2 | 1/2006 |
| WO | WO 2006/046699 | | 5/2006 |
| WO | WO 2007102785 | A1 * | 9/2007 |
| WO | WO 2008/063136 | | 5/2008 |
| WO | WO 2010/120249 | A1 | 10/2010 |
| WO | WO 2012/011877 | A2 | 1/2012 |

OTHER PUBLICATIONS

Supplementary Search Report for EP 07 83 5548 dated Jun. 30, 2010.
International Search Report and Written Opinion dated Feb. 20, 2008 for International Application No. PCT/SG2007/000393.
International Search Report and Written Opinion dated May 8, 2006 for International Application No. PCT/SG2006/000050.
International Search Report and Written Opinion dated Feb. 29, 2012 for International Application No. PCT/SG2011/000263.
International Search Report and Written Opinion dated Sep. 17, 2010 for International Application No. PCT/SG2011/000153.
Asberg, et al., "Surface Energy Modified Chips for Detection of Conformational States and Enzymatic Activity in Biomolecules" (2006) Langmuir 22, 2205-2211.
Beck, et al , "Improving stamps for 10 nm level wafer scale nanoimprint lithography" (2002) Microelectron Engineering 61-62, 441-448.
Benor, et al., "Microstructuring by microcontact printing and selective surface dewetting" (Jul./Aug. 2007) Journal of Vacuum Science & Technology B, 25 (4) 1321-1326.
Beste, et al., "Small antibody-like proteins with prescribed ligand specificities derived from the lipocalin fold" (Mar. 1999) Proc. Natl. Acad. Sci. USA 96, 1898-1903.
Biffinger, et al., "The Polar Hydrophobicity of Fluorinated Compounds" (2004) ChemBioChem 5, 622-627.
Burbulis, et al., "Quantifying small numbers of antibodies with a 'near-universal' protein-DNA chimera" Nature Methods (2007 DOI: 10.1038/NMETH1127).
Chiriac, et al., "Magnetic GMI sensor for detection of biomolecules" (2005) Journal of Magnetism and Magnetic Materials 293, 671-676.
Churaev, et al., "Wetting of low-energy surfaces" (2007) Advances in Colloid and Interface Science 134-135, 15-23.
Daniel, et al., "Vibration-Actuated Drop Motion on Surfaces for Batch Microfluidic Processes" (2005) Langmuir 21, 4240-4248.
Dill, et al, "Modeling Water, the Hydrophobic Effect, and Ton Solvation" (2005) Annu. Rev. Biophys. Biomol. Strict. 34, 173-199.
Gao et al., "A Commercially Available perfectly Hydrophobic Material ($O_A/O_R = 180°/180°$)" (Aug. 28, 2007) Langmuir, 23, 18, 9125-9127.
Gascoyne, et al., "Dielectrophoresis-based programmable fluidic processors" (2004) Lab Chip 4, 299-309.
Genua, et al., "Functional patterns obtained by nanoimprinting lithography and subsequent growth of polymer brushes" (2007) Nanotechnology 18, 215301 (7 pages).
Gill et al., "Biopharmaceutical drug discovery using novel protein scaffolds" (2006) Current Opinion in Biotechnology 17, 653-658.
Giovambattista, et al., "Effect of Surface Polarity on Water Contact Angle and Interfacial Hydration Structure" (2007) J. Phys. Chem B. 111, 9581-9587.
Goddard & Hotchkiss, "Polymer surface modification for the attachment of bioactive compounds" (2007) Progress Polymer Science 32, 698-725.
Griffiths & Tawfik, "Miniaturising the laboratory in emulsion droplets" (2006) Trends in Biotechnology 24, 9, 395-402.
Herrmann, et al, "Enzymatically-generated fluorescent detection in micro-channels with internal magnetic mixing for the development of parallel microfluidic ELISA" (2006) Lab Chip 6, 555-560.
Holt, et al., "Domain antibodies: proteins for therapy" (Nov. 2003) Trends in Biotechnology 21, 11, 484-490.
Hutten, et al., "New magnetic nanoparticles for biotechnology" (2004) J. Biotech. 112, 47-63.
Iliades, et al, "Triabodies: single chain Fv fragments without a linker form trivalent trimers" (1997) FEBS Letters 409, 437-441.
Jakobs and Hanein, "Micrometer scale gel patterns" (2006) Colloids and Surfaces A: Physciochem. Eng. Aspects 290, 33-40.
Jung & Bhushan, "Wetting transition of water droplets on superhydropbobic patterned surfaces" (2007) Scripta Materialia 57, 1057-1060.
Kanta, et al., "Preparation of Silica-on-Titania Patterns with a Wettability Contrast" (2005) Langmuir 21, 5790-5794.
Kusumaatmaja, et al., "Controlling Drop Size and Polydispersity Using Chemically Patterned Surfaces" (2007) Langmuir 23, 956-959.

(56) References Cited

OTHER PUBLICATIONS

Kwon, et al., "Quantitative Evaluation of the Relative Cell Permeability of Peptoids and Peptides" (2007) J. Am. Chem. Soc. 129, 1508-1509.
Li, et al., "What do we need for a superhydrophobic surface? A review on the recent progress in the preparation of superhydrophobic surfaces" (2007) Chem. Soc. Rev. 36, 1350-1368.
Luca, D., "Preparation of TiOx Thin Films by Reactive Pulsed-Laser Ablation" (Apr. 2005) Journal of Optoelectronics and Advanced Materials, vol. 7, No. 2, 625-630.
Lundgren, et al., "Modeling of Wetting: A Study of Nanowetting at Rough and Heterogeneous Surfaces" (2007) Langmuir 23, 1187-1194.
Ma & Hill, "Superhydropliobic surfaces" (2006) Current Opinion in Colloid & Interface Science 11, 193-202.
Mardare et al., "Microelectrochemical lithography: A method for direct writing of surface oxides" (2007) Electrochimica Acta 52, 7865-7869.
Matsuda, et al., "Phosphorylcholine-endcapped oligomer and block co-oligomer and surface biological reactivity" (2003) Biomaterials 24, 4517-4527.
Meyer, et al., "Recent progress in understanding hydrophobic interactions" (Oct. 24, 2006) PNAS 103, 43, 15739-15746.
Mosavi, et al., "The ankyrin repeat as molecular architecture for protein recognition" (2004) Protein Science 13, 1435-1448.
Opdahl, et al., "Polymer Surface Science" (2001) The Chemical Record vol. 1, 101-122.
Pollack, et al., "Electrowetting-based actuation of liquid droplets for microfluidic applications" (2000) Appl. Phys. Lett. 77, 11, 1725-1726.
Popp, et al., "Sortagging: a versatile method for protein labeling" (2007) Nature Chemical Biology 3, 11, 707-708.
Rastogi, et al., "Development and evaluation of realistic microbioassays in freely suspended droplets on a chip" (2007) Biomicrofluidics 1, 014107-1-014107-17.
Roach, et al., "Controlling Nonspecific Protein Adsorption in a Plug-Based Microfluidic System by Controlling Interfacial Chemistry Using Fluorous-Phase Surfactants" (2005) Anal. Chem. 77, 785-796.
Ronaghi, M., "Pyrosequencing Sheds Light on DNA Sequencing" (2001) Genome Research 11, 3-11 (www.genome.org).
Rose, D., "Microdispensing technologies in drug discovery" (Sep. 1999) Drug Discovery Today vol. 4, No. 9, 411-419.
Satriano, et al., "Bacterial adhesion onto nanopatterned polymer surfaces" (2006) Materials Science & Engineering C 26, 942-946.
Silverman, et al., "Multivalent avimer proteins evolved by exon shuffling of a family of human receptor domains" (Dec. 2005) Nature Biotechnology V. 23, No. 12, 1556-1561.
Skerra, A., "Engineered protein scaffolds for molecular recognition" (2000) J. Mol. Recognit. 13, 167-187.
Song, et al., "Miniature biochip system for detection of *Escherichia coli* O157:H7 based on antibody-immobilized capillary reactors and enzyme-linked immunosorbent assay" (2004) Analytical Chimica Acta 507, 115-121.
Stephenson, et al, "Quantifying the hydrophobic Effect. 1. A Computer Simulation-Molecular-Thermodynamic Model for the Self-Assembly of Hydrophobic and Amphiphilic Solutes in Aqueous Solution" (2007) J. Phys. Chem. B. 111, 1025-1044.

Stone, et al, "The assembly of single domain antibodies into bispecific decavalent molecules" (2007) Journal of Immunological Methods 318, 88-94.
Sundberg, et al., "Contact angle measurements by confocal microscopy for non-destructive microscale surface characterization" (2007) J. Colloid and Interface Science 313, 454-460.
Van Oss, et al., "Long-range and short-range mechanisms of hydrophobic attraction and hydrophilic repulsion in specific and aspecific interactions" (2003) J. Mol. Recognit. vol. 16, 177-190.
Wang, et al., "In Situ Wilhelmy Balance Surface Energy Determination of Poly(3-hexylthiophene) and Poly(3, 4-ethylenedioxythiophene) during Electrochemical Doping-Dedoping" (2006) Langmuir, vol. 22, 9287-9294.
Wang, et al., "Flow-Focusing Generation of Monodisperse Water Droplets Wrapped by Ionic Liquid on Microfluidic Chips: From Plug to Sphere" (2007) Langmuir, vol. 23, 11924-11931.
Washizu, M., "Electrostatic Actuation of Liquid Droplets for Microreactor Applications" (Jul./Aug. 1998) IEEE Transactions on Industry Applications, vol. 34, No. 4, 732-737.
West, et al., "Microplasma writing for surface-directed millifluidics" (2007) Lab Chip, vol. 7, 981-983.
Widom, et al, "The hydrophobic effect" (2003) Phys. Chem. Chem. Phys. vol. 5, 3085-3093.
Wixforth, et al., "Flatland fluidics" (2002) MST News, No. 5, 42-43.
Agency for Science, Technology and Research, International Preliminary Report on Patentability, PCT/SG2007/000393, May 26, 2009, 4 pgs.
Agency for Science, Technology and Research, Notification of Reasons for Refusal, JP 2009-538373, Nov. 10, 2011, 7 pgs.
Agency for Science, Technology and Research, Notification of Reasons for Refusal, JP 2012-196318, Dec. 10, 2013, 3 pgs.
Agency for Science, Technology and Research, Notification of the First Office Action, CN 200780048922.8, Nov. 12, 2010, 4 pgs (available in Chinese only).
Agency for Science, Technology and Research, Notification of the Second Office Action, CN 200780048922.8, May 17, 2011, 4 pgs.
Agency for Science, Technology and Research, Notification on the Grant of Patent Right for Invention, CN 200780048922.8, Sep. 22, 2011, 1 pg.
Curiox Biosystems Pte Ltd, International Preliminary Report on Patentability, PCT/SG2010/000153, Oct. 18, 2011, 15 pgs.
Curiox Biosystems Pte Ltd, International Preliminary Report on Patentability, PCT/SG2011/000263, Dec. 21, 2012, 5 pgs.
Curiox Biosystems Pte Ltd, International Search Report and Written Opinion, PCT/IB2013/000623, Jul. 10, 2013, 7 pgs.
Kim, Notice of Allowance, U.S. Appl. No. 12/282,162, May 14, 2012, 7 pgs.
Kim, Office Action, U.S. Appl. No. 12/282,162, Jun. 27, 2011, 8 pgs.
Leck, Final Office Action, U.S. Appl. No. 11/984,197, May 8, 2012, 10 pgs.
Leck, Office Action, U.S. Appl. No. 11/984,197, Mar. 14, 2013, 11 pgs.
Leck, Office Action, U.S. Appl. No. 11/984,197, May 26, 2011, 11 pgs.
Leck, Office Action, U.S. Appl. No. 11/984,197, Jul. 31, 2013, 12 pgs.

* cited by examiner

Cover moves forward towards the plate. When in place, the plate holder moves upwards to force the plate against the cover, thereby making a tight seal against a gasket and forming a water tight chamber.

Tilting Action at 0, 90 and 120 degree

Tilt at 0 degree for loading/unloading and washing

Tilt at 90 degree for addition of wash buffer

Tilt at 120 degree draining wash buffer and oil

USE OF CHEMICALLY PATTERNED SUBSTRATE FOR LIQUID HANDLING, CHEMICAL AND BIOLOGICAL REACTIONS

PRIORITY

This patent application is a 371 United States national stage conversion of International Patent Application Serial No. PCT/SG2010/000153, filed Apr. 17, 2010, entitled, "Use of Chemically Patterned Substrate for Liquid Handling, Chemical and Biological Reactions", and naming Namyong Kim, Kong Leong Cheng, Li Li, and Teow Soon Seah as inventors which itself claims priority from provisional U.S. patent application No. 61/170,201, filed Apr. 17, 2009 entitled, "Use of Chemically Patterned Substrate for Liquid Handling, Chemical and Biological Reactions," and naming Namyong Kim, Kong Leong Cheng, and Li Li as inventors, the disclosures of each of which are incorporated herein, in their entirety, by reference.

FIELD OF THE INVENTION

The invention generally relates to systems and methods for handling small volumes of liquids and, more particularly, the invention relates to systems and methods for facilitating assays in small volumes.

BACKGROUND OF THE INVENTION

Biological, biochemical and chemical analyses are often performed in a microplate format. Standard format microplates are promulgated by the Society for Biomolecular Screening (SBS). Of these, 96-well, 384-well, and 1536-well microplates are commonly used in scientific, analytical, and diagnostic pursuits. The SBS format enjoys an ecosystem of instrumentation suppliers for automated liquid handling, incubation, plate reading, plate storage and plate handling.

An alternate microwell format based on hydrophobic/hydrophilic patterning together with associated methods and instrumentation is described in WO2008/063136, published May 29, 2008. That publication also describes methods and devices for performing inhomogeneous assays using the format. This format combines advantages of microarrays and microplates. For example the format allows for parallel washing of adhered samples at high throughput. Arrays with hydrophilic elements in a hydrophobic background are available commercially; e.g., PTFE printed slides from TEKDON, Myakka City, Fla., USA.

SUMMARY OF THE INVENTION

In accordance with one aspect of the invention, there is a holder for holding a liquid handling plate. The holder includes a generally rectangular frame sized to hold the plate and having a circumferential side wall. At least one portion of the side wall of the frame has a sloping feature having a slope such that when a plate is mounted in the frame to form a mounted structure and a liquid is held in the mounted structure so as to contact the frame in a draining position, gravity will cause the liquid to be drawn downward along the slope.

Embodiments of the invention include additional or optional features. In one such embodiment, an identification feature suitable for communication with an automated instrument for washing the mounted structure is usable to authenticate the source of the plate, to control the plate washing process by setting one or more parameters such as a first type of wash buffer, a first volume of wash buffer, a first shaking duration, a first shaking speed, a first rest duration before draining, a first draining duration, a first draining angle a second wash buffer, a second wash volume, a second shaking duration, a second shaking speed, a second rest duration before draining, a second draining duration, and a second draining angle, to confirm that the plate is mounted on the machine in a safe or desired location, to identify the number or arrangement of hydrophilic features on the plate, and/or to record the date of production of the plate, the date of expiry of the plate, or the number of times the plate has been washed. The identification feature is optionally a writable feature such as an RFID device operable to store information written by the machine such as an update to the number of times the plate has been washed.

Furthermore, in accordance with related embodiments, the holder may comprise a plurality of feet sized to elevate the plate by a fixed amount to thereby create a gap which enhances the parallel positioning of the plate relative to the holder when a sealant such as an adhesive or elastomer is positioned in the gap.

In accordance with related embodiments, the holder may also comprise a raised portion mounted atop the side wall for sealingly contacting a cover when pressed against a gasket, the raised portion preferably positioned near the inside edge of the side wall.

In accordance with a specific embodiment, there is the holder together with the plate, where the plate further comprising an array of hydrophilic regions in a hydrophobic background, the hydrophilic regions are preferably arranged with an industry standard microplate spacing, and the plate is preferably positioned with a flatness of less than 200 micrometers over the area of the plate.

In accordance with a further specific embodiment, the holder further comprises at least one cutout positioned to mechanically signal information to an array of switches on a receiving platform of a corresponding plate washing instrument.

In accordance with another embodiment of the invention, there is a liquid handling plate that comprises an array of hydrophilic regions in a hydrophobic background. The hydrophilic regions are preferably arranged with an industry standard microplate spacing. The plate also includes an array holder for mounting the array and an identification feature suitable for communication with an automated instrument for washing the mounted structure to perform an assay.

In a related embodiment, the identification feature carries information usable by a plate washing machine. The information can be usable by the plate washing machine to authenticate the source of the plate, to control the plate washing process by setting one or more parameters such as a first type of wash buffer, a first volume of wash buffer, a first shaking duration, a first shaking speed, a first rest duration before draining, a first draining duration, a first draining angle a second wash buffer, a second wash volume, a second shaking duration, a second shaking speed, a second rest duration before draining, a second draining duration, and a second draining angle, to confirm that the plate is mounted on the machine in a safe or desired location, to identify the number or arrangement of hydrophilic features on the plate, and/or to record the date of production of the plate, the date of expiry of the plate, or the number of times the plate has been washed. The identification feature is optionally a writable feature such as an RFID device operable to store information written by the machine such as an update to the number of times the plate has been washed.

In a related embodiment, the plate comprises a raised portion atop the side wall, for sealingly contacting a cover when pressed against a gasket, the raised portion preferably positioned near the inside edge of the side wall.

In a further related embodiment, the plate includes a support grid adapted to support the substrate in a generally planar position and preferably having openings aligned with the hydrophilic regions so as to permit optical interrogation thereof.

In a further related embodiment there is a system, including the above-mentioned plate together with a plate washing machine operable to extract information from and optionally write information to the identification feature. The identification feature may comprise a cutout positioned for actuating an array of switches on a receiving platform of a plate washing machine.

In accordance with another embodiment of the invention, there is a fluid-exchange cover for sealingly covering a fluidic plate. The cover includes a fluidic channel system comprising one or both of an oil inlet in fluid communication with an oil outlet and, optionally, an air vent, arranged so that when the cover is held sealingly against a fluidic plate having a wall, fluid injected into the inlet is directed against the wall in a manner that does not disrupt liquid adhered to hydrophilic regions of the plate; and a washing liquid inlet in communication with a branched channel structure that divides the flow of washing liquid injected into the channel so as to lessen a potential impact of the washing liquid against the hydrophilic elements.

In accordance with another embodiment of the invention, there is a method for controlling a residual volume of an aqueous solution bathing an array comprising a plurality of hydrophilic elements on a hydrophobic background. The method comprises adding an aqueous liquid so as to contact the hydrophilic elements, tilting the array to a selected angle from a horizontal reference plane, (wherein the angle is less than 120 degrees and preferably between 5 degrees and 115 degrees, more preferably between 15 and 90 degrees), and allowing the aqueous liquid to drain while leaving a residual volume adhered to the elements.

In a related embodiment, the method comprises selecting a desired residual volume and selecting a corresponding angle so as to leave behind the desired residual volume.

In accordance with another embodiment of the invention, there is a device for holding an array of liquid aqueous liquid droplets. The device comprises a pattern of hydrophilic liquid-capturing elements on a hydrophobic background, the hydrophobic background coated by a layer of hydrophobic liquid that imparts additional nonwetting characteristics to the hydrophobic background when challenged with an aqueous liquid. The hydrophobic liquid is immiscible with the aqueous liquid and, preferably, the surface tension of the hydrophobic liquid is equal to or greater than the surface tension of the hydrophobic background and the surface tension of the immiscible liquid is lower than that of the aqueous liquid.

In related embodiments, the aqueous liquid may be phosphate buffered saline. The immiscible liquid may have a kinematic viscosity of less than 20 cSt, and preferably less than 15 cSt. The layer of hydrophobic liquid may be less than 5 mm thick and preferably less than 1 mm thick. The immiscible liquid may comprises a perfluorocarbon, preferably having a vapor pressure low enough to allow use of the device without exposing the hydrophobic background for 2 or more hours. The device may be packaged to prevent gas exchange, preferably so as to maintain the immiscible liquid for 6-12 months or more. The device may have a roughened hydrophobic background, preferably characterized by an rms roughness of 50-100 micrometers or greater.

In accordance with another embodiment of the invention, there is a method for protecting an array of hydrophilic elements on a hydrophobic background from wetting by a hydrophobic liquid introduced to the array. The method includes selectively coating the hydrophobic background with a layer of hydrophobic liquid that imparts additional nonwetting characteristics to the hydrophobic background when challenged with an aqueous liquid. The hydrophobic liquid is immiscible with the aqueous liquid and, preferably, the surface tension of the hydrophobic liquid is equal to or greater than the surface tension of the hydrophobic background and the surface tension of the immiscible liquid is lower than that of the aqueous liquid.

In a related embodiment, the aqueous liquid may be phosphate buffered saline. The immiscible liquid may have a kinematic viscosity of less than 20 cSt, and preferably less than 15 cSt. The immiscible liquid may comprise a perfluorocarbon, preferably having a vapor pressure low enough to allow use of the device without exposing the hydrophobic background for 2 or more hours. The method may include using a roughened hydrophobic background, the roughness of the hydrophobic background sufficient to prevent outmigration of immiscible liquid and preferably characterized by an root mean squared roughness of 50-100 micrometers or greater. The roughness of the hydrophobic background, viscosity of the immiscible liquid, surface tension of the background, and surface tension of the immiscible liquid may be chosen so that immiscible liquid remains on the hydrophobic portions of the surface and does not block attachment of the aqueous liquids to the hydrophilic elements. The method may further include performing an assay.

In accordance with another embodiment of the invention, there is a frame for holding a deformable transparent microfluidic substrate. The frame comprises a plurality of support pillars positioned to hold the substrate in a flat configuration. The pillars are preferably separated by cutout portions.

In a related embodiment, the pillars are rounded and/or hydrophobic to reduce the potential for wetting of the pillars. A device may further comprise the substrate, where the substrate optionally has a plurality of spaced apart hydrophilic elements in a hydrophobic background.

In accordance with another embodiment of the invention, there is an assay array comprising a deformable microfluidic substrate in a generally planar configuration, a generally rectangular border extending normal to the plane of the substrate, and a supporting grid below the substrate, the substrate preferably having an array of hydrophilic elements in a hydrophobic background and the grid preferably having openings aligned with the hydrophilic elements to permit optical transmission through both the grid and the hydrophilic elements.

In accordance with another embodiment of the invention, there is a device for washing a microfluidic array assembly having an array of liquid droplets adhered thereto. The device comprises a mechanism for draining a hydrophobic liquid from the assembly, a mechanism for filling the assembly with an aqueous wash liquid; a mechanism for shaking the assembly in the presence of the aqueous wash liquid; a mechanism for tilting and thereby draining the wash liquid from the assembly; and a spill sensor placed under the assembly to trigger an alarm condition if the spill sensor is contacted by wash liquid.

In accordance with another embodiment of the invention, there is a device for washing a microfluidic array assembly having an array of liquid droplets adhered thereto. The device comprises a mechanism for draining a hydrophobic liquid from the assembly, a mechanism for filling the assembly with an aqueous wash liquid; a mechanism for shaking the assembly in the presence of the aqueous wash liquid; a mechanism for tilting and thereby draining the wash liquid from the assembly; an optional spill sensor placed under the assembly to trigger an alarm condition if the spill sensor is contacted by wash liquid; and a reader adapted to read information from the assembly and to use the information to authenticate the source of the plate, to control the plate washing process by setting one or more parameters such as a first type of wash buffer, a first volume of wash buffer, a first shaking duration, a first shaking speed, a first rest duration before draining, a first draining duration, a first draining angle a second wash buffer, a second wash volume, a second shaking duration, a second shaking speed, a second rest duration before draining, a second draining duration, and a second draining angle, to confirm that the plate is mounted on the machine in a safe or desired location, to identify the number or arrangement of hydrophilic features on the plate, to record the date of production of the plate, to record the date of expiry of the plate, and/or to record the number of times the plate has been washed. Optionally, the device includes a writing device for use with a writable identification feature such as an RFID device the writing device operable to store information on the identification feature such as an update to the number of times the plate has been washed.

Illustrative embodiments of the invention are implemented as a computer program product having a computer usable medium with computer readable program code thereon. The computer readable code may be read and utilized by a computer system in accordance with conventional processes.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

FIG. 1b shows a perspective underside view of the plate/holder assembly of FIG. 1a;

DESCRIPTION OF ILLUSTRATIVE EMBODIMENTS

In illustrative embodiments, methods and devices allow for effective, efficient and flexible use of patterned fluidic elements. Details of illustrative embodiments are discussed below.

Embodiments of the invention feature or use a patterned hydrophobic/hydrophilic fluidic sample array. Preferably, the substrate is flat and has hydrophilic elements that are capable of holding a hydrophilic liquid volume. In a specific embodiment, the substrate is a glass slide that is patterned with a hydrophobic coating. The hydrophobic coating leaves an array of uncoated regions of glass that act as the hydrophilic elements. The hydrophilic elements may further be coated with hydrophilic coatings to promote specific binding, to discourage nonspecific binding, or both. The held volume is most commonly aqueous, but could also comprise another polar solvent, such as DMSO but, for simplicity, the embodiments refer to aqueous samples. The plate can be a glass plate. The hydrophobic regions can be applied to a glass plate by printing a hydrophobic coating or other suitable method. The hydrophobic regions may be fluorinated or perfluorinated. For example, these may be composed of Teflon® or related material. Optionally, the hydrophilic regions may be coated to increase hydrophilicity, prevent nonspecific binding, present binding probes, or support the adhesion and/or health of cells.

Preferably, the hydrophobic regions are arranged on a standard format, such as that for a 96, 384, or 1536 well microplate, or subregion thereof.

As described in WO2008/063136, aqueous samples may be dispensed so that they adhere to the hydrophilic regions. By virtue of its lacking microplate well walls that block transfer of fluid from element to element, the plate may be easily washed by an aliquot or flow of liquid, and excess liquid can easily be drained; e.g., using gravity. A low surface energy liquid may be used to rinse the plate with adhered samples to prevent sample carryover and crosstalk and to cover the adhered samples to prevent evaporation during incubation and analysis. One such fluid is Fluorinert (from 3M). A mixture of perfluoro and hydrofluoro-compounds (bp 180-230° C.) suitable for this purpose is also available from Curiox Biosystems ("Rinsing Oil"). The system is especially useful for inhomogeneous assays that require binding steps, including cell adhesion, certain nucleic acid assays, and immunoassays. In a preferred embodiment, the surface tension of the hydrophobic coating is less than or equal to the surface tension of the rinsing oil, which is in turn less than the surface tension of the aqueous liquid, which is in turn less than the surface tension of hydrophilic surface.

Figure 1A:
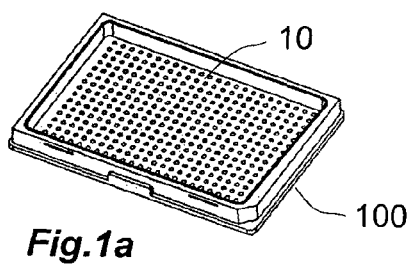
FIG. 1a shows a perspective top view of a plate/holder assembly, in accordance with an embodiment of the invention.
Figure 1B:
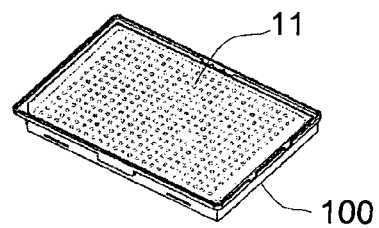
Figure 1C:
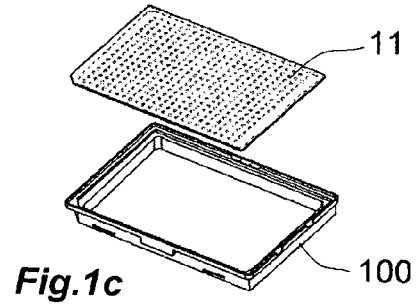
FIG. 1c shows a perspective exploded view of the plate/holder assembly of FIGS. 1a-1b.

FIGS. 1a-1c shows a microfluidic plate assembly 10 having a plate 11 with hydrophilic elements in a hydrophobic background and a plate holder 100. The example shown has 384 elements, in the general format of a microplate. In various embodiments, other formats may be used, including a microscope-slide type format, as described below.

Figure 2A:
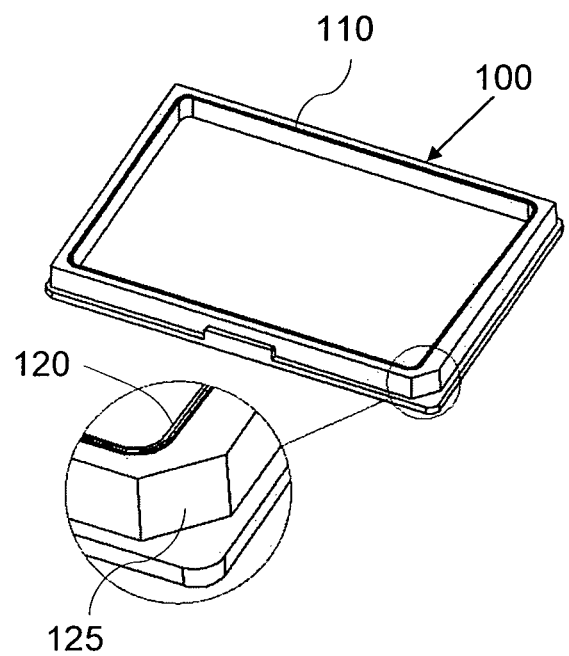
FIG. 2a shows a top perspective view of a plate holder having an upper ridge in accordance with an embodiment of the invention.

FIG. 2a shows a top perspective view of a holder 100 that can be used to hold or frame a fluidic plate 11, for ease of manual or automatic handling, in accordance with an embodiment of the present invention. The plate may have a hydrophobic/hydrophilic pattern as mentioned above, but other microfluidic structures may also benefit from using the holder 100. For low cost, the holder 100 can be made of injection molded plastic, such as polypropylene. The holder 100 can have a generally rectangular shape and can be dimensioned to be compatible with industry standard microplate handling equipment. Alternately, the holder can be dimensioned in a microscope slide format. Other formats are possible. The holder 100 has a circumferential side wall 110. When a plate is mounted in the holder 100, the plate and the wall 110 may form a leak-resistant chamber so that various fluids may be introduced.

In an embodiment, the holder 100 is usable with a cover. The holder 100 may include a raised portion 120, preferably in the form of a rounded bump atop the holder wall 110. An advanced cover design is described below in connection with FIGS. 8-11, but other covers, including simpler designs may be used. The cover may include a resilient gasket that is dimensioned to be complementary to the raised portion 120 so that when the cover is pushed against the holder, a leak-resistant chamber is formed. It is advantageous to place the raised portion toward the inside edge of the side wall 110 to avoid creating a capillary encircling the junction of the side wall 110 and the cover, because the capillary will fill with liquid during use. Optionally, the holder may include a flat corner 125 to act as an orientation reference.

Figure 2B:
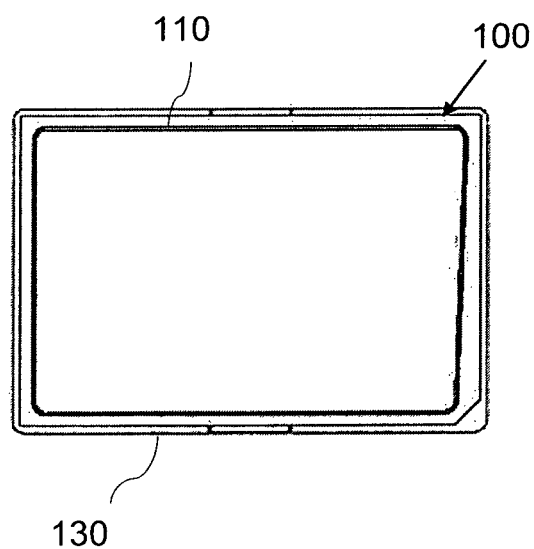
FIG. 2b shows a plan view of a plate holder having a drainage slope, in accordance with an embodiment of the invention.

FIG. 2b shows a schematic plan view of the holder 100, in accordance with an embodiment of the invention. At least one portion of the side wall 110 forms a slope 130. In use, the holder 100 can at times include a fluidic plate (typically attached to the bottom of the holder 100), with a cover applied (typically to the top of the holder 100), and a liquid held therebetween. For example, the holder/plate will be in this condition when the plate is being washed. The slope 130 is of sufficient angle that when the holder/plate/cover system is tilted from the horizontal (e.g. at 90 degrees) and an outlet is provided near the lowest point of the system, the liquid will drain more effectively than if the holder 100 were perfectly rectangular. In other words, the last drops of draining liquid will flow down the slope and into the drain, thus reducing the residual liquid volume in the system. The slope may be, for example, 1 to 10 degrees, or more. The draining may be passive, using gravity, or active, using suction or centrifugation. The filling and/or draining operations may be performed by an automated instrument.

Figure 3:
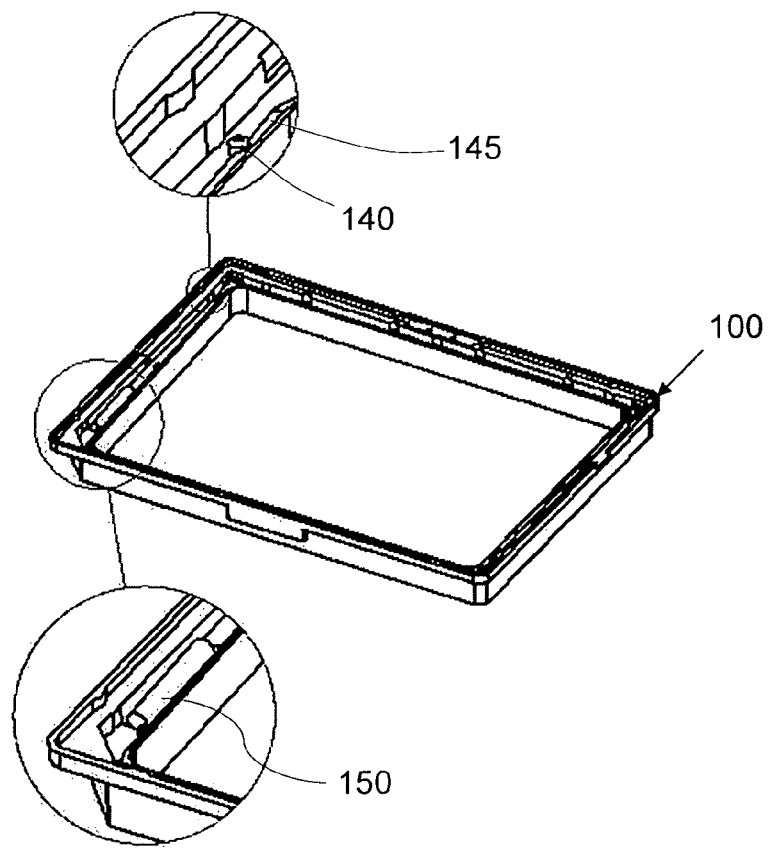
FIG. 3 shows a bottom perspective view of a plate holder having a plate leveling feature and an identification feature in accordance with an embodiment of the invention.

FIG. 3 shows a bottom view of the holder 100 having a leveling feature in the form of small feet 140 and a plate identification feature 150. The feet 140 may protrude from a lip 145 and may protrude on the order of, for example, 0.2-0.4 mm. The feet allow for level attachment of a microfluidic plate to the holder 100. By offsetting the plate from a supporting portion of the holder 100, variations in plate high due to the use of a sealant between the plate and the holder 100 are minimized. The sealant may be, for example, and adhesive such as glue or an adhesive tape, or may be an elastomer (in which case the plate can be pressed against the elastomer to for a seal). The use of solid feet 140 causes the plane of attachment of the plate to be determined by the feet rather than the sealant. Preferably, the seal is leakage-resistant. Preferably, the flatness of the plate is 200 micrometers or less in deviation from the average elevation over the area of the plate.

The identification feature is a machine readable identifier such as a bar code or radio frequency tag identity tag (RFID) or other such component. The identifier may also have a write-feature, as in the case of an RFID, which allows a machine to record information thereupon.

When a disposable plate designed for running multiple, specific reactions is introduced to a designated instrument (e.g., a machine for washing the plate), it can be beneficial to identify one or more characteristics of the incoming plate accurately. Such recognition avoids potential confusion in the process, which could lead to wrong information in the end. It is desirable to introduce simple and easy markings and recognize the nature of a plate in order to run a process rightfully programmed for the plate.

At present, many solutions are available for identifying the plate. However, often a recognizing mark such as barcode sticker is introduced by a user during a secondary processing of the plates rather than at the manufacturing stage. Such practice leaves open the possibility of confusing plates made from different manufacturing processes.

The plate holder 100 can have a small pocket along its wall 110, which is used for embedding a RFID tag 150. The RFID tag 150 can be used for recording information about the plate, such as the plate type, batch number, date of production, etc. The purpose of RFID (Radio Frequency Identification) is to achieve one or more of the following:

To establish the authenticity of the product used in order to maintain the quality of the results To record product information To enable automated instrument to extract operational parameters from the RFID and run an optimal process for the particular plate To ensure safe operation of the instrument by confirming the presence of a plate in a desired location The RFID communication allows for non-contact information exchange established between a RFID tag and a RFID reader or reader/writer. The RFID tag may have its own unique ID. Other than the unique ID, the device can have a readable/writable digital memory (e.g., 1 to 100 bytes or more). The data in the memory may be encoded to include some or all of the following information:

1. Type of the consumable (e.g., 1 for a 384 feature cell analysis plate, 2 for 384-feature ELISA plate, etc.)
2. Date of production
3. Batch number
4. Date of Expiry, if any
5. Operational parameters, such as:
   a. type of wash buffer (for instruments that support such choice, otherwise instrument will ignore and use what is available)
   b. volume of wash buffer
   c. shaking duration
   d. shaking speed
   e. rest duration before drain
   f. drain duration
   g. 2nd type wash buffer
   h. volume of 2nd wash buffer
   i. 2nd shaking duration
   j. 2nd shaking speed
   k. 2nd rest duration before drain
   l. 2nd drain duration
6. number of times used (which is instrument writable data)
7. A code/algorithm for a washing instrument to establish authenticity An RFID reader/writer can be integrated device in the washing instrument that does one or more of the following:

1. When a consumable product, for example a plate, is placed onto an automated instrument plate handling instrument, the RFID reader can establish the presence of the plate and authenticity of the plate through the code. The confirmation of the presence of the plate is important because the operation of the instrument without the plate in place may result in serious safety breach due to mechanical and electrical hazard, and/or from flooding of liquid reagents in the absence of the plate. RFID communication will avoid the accidental run of the instrument without the plate in place.
2. The RFID reader will check the number of times the consumable is washed. If the number of times washed is more than a specified quantity, the reader will issue a warning to the instrument controller to alert the user.
3. If the instrument has an internal clock, it may compare the expiry date to the current date. If the expiry is reached, it may issue a warning to the instrument controller to alert the user.
4. Upon meeting the conditions as stated above, the reader can extract operational parameters from the RFID tag. These parameters will then be sent to the instrument controller, where the controller will use this information to run the operations.
5. Upon the end of a washing operation, the RFID reader, which may also be a writer, of the instrument can change the code for the number of times washed in the RFID tag to indicate 1 more time washed.
6. Upon the end of step 5, the RFID reader will issue an end of operations instruction to the instrument controller to alert the user, or in the case of a fully automated system, the system controller to pick up the consumable.

The detection of a plate by physical contact is particularly useful for running a washing process. A washing instrument is designed to run a washing process when a plate is delivered to the instrument by a user or an automated system. When the plate is not properly positioned on the plate stage (or holder), neither contact sensor is pressed. This may alarm the instrument not to start the washing process. Likewise, when a plate is missing from the instrument by mistake, the washing instrument can be programmed to not start the process, which could otherwise lead to disastrous circumstances. In addition, the differentiation of different plate types is useful by assuring to run a right washing process for the type of a plate introduced. For example, the washing instrument may distinguish between ELISA and cell plates and select an appropriate washing protocol. A user may program to run cell washing process for an ELISA plate or vice versa. In such a case, the washing instrument stops the process and generates an error message before proceeding to the next step.

The RFID recognition method is potentially expensive (although costs are falling). Accordingly, in an alternate embodiment a contact sensor may offer similar advantages by providing a simple, effective solution to prevent the confusion of plates designed for different processes. The plate or plate holder itself is manufactured with a physical key feature such as indented marking or tracking features. The amount of information to be stored in a plate requires different level of tracking feature. For example, to achieve a simple differentiation with four different variables, physical indentation in a plate can be a best method to achieve. If the level of information requires more than 10 different variables, a method like RFID can be employed in order to carry such information.

Figure 4:
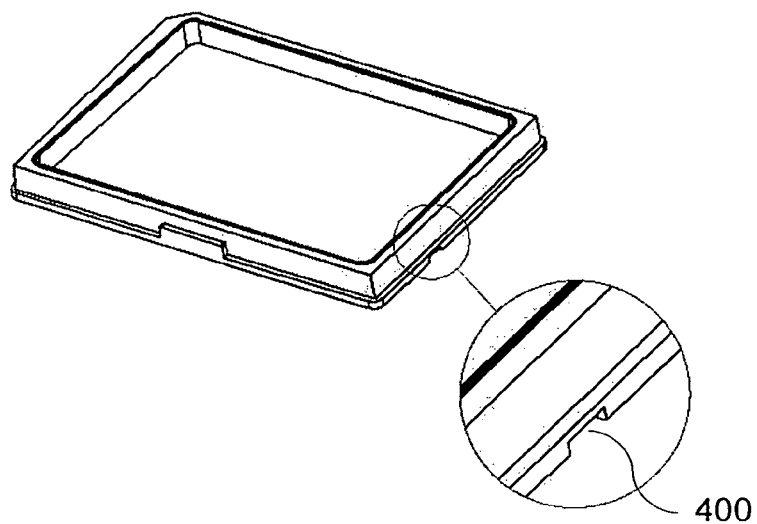
FIG. 4 shows a top perspective view of a plate holder having a physical key feature in accordance with an embodiment of the invention.

FIG. 4 shows a plate holder 100 with a physical key-feature. The key-feature may be an indentation our cutout in a plate, which can be recognized by an accepting instrument (e.g., the plate washing instrument described below). One or more cutouts can be made along the edge of the plate holder wall 110 at the size of 2-10 mm. The location of the cutout along the edge is used for making identification of the plate. Two or more cutouts or other features may be used on a single plate, depending on the corresponding receiving platform of a plate washing instrument which may have an array of two or more contact switch/sensors for determination of plate identity.

Figure 5:
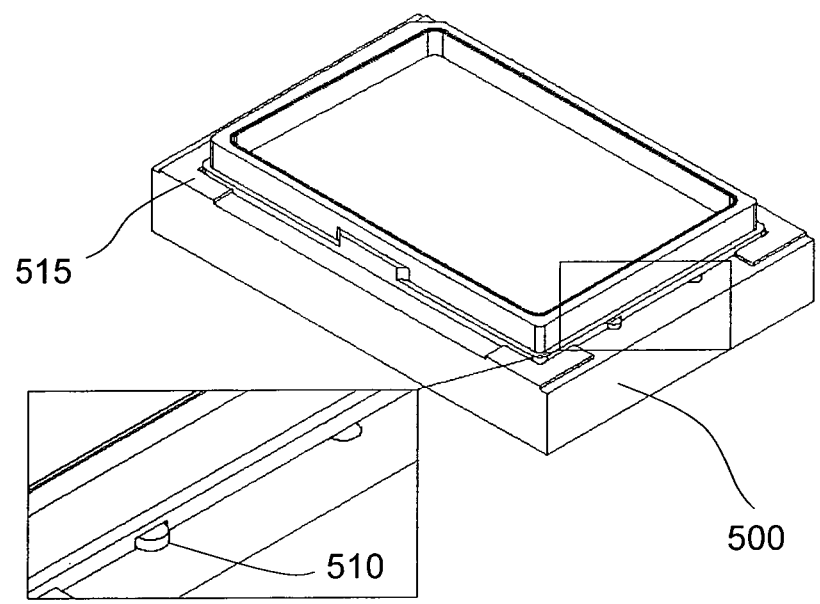
FIG. 5 shows a top perspective view of the plate holder of FIG. 4 mounted on a platform of a washing instrument, in accordance with an embodiment of the invention.

FIG. 5 shows the plate loaded onto a receiving platform 500 for certain operations. Alignment features 515 on the platform 500 ensure the plate is placed correctly. The platform has a series of sensors (e.g. switches) 510. Depending on the location of the cutout or cutouts, a different pattern of switches 510 is triggered. A combination of the switch/sensor activation determines the identification of the plate, as well as the state of plate loading action, and determines if a plate is present. If no plate is present, none of the switches/sensors 510 will be activated.

The contact sensors 510 can differentiate, for example, the presence and absence of a plate and ELISA or cell assay type plate when a place is present. If both contact sensors 510 are free, it means that there is no plate. This can prevent accidental triggering of a program when a plate is missing by mistake. The washing instrument that accepts the plate assembly may feature a controller programmed to activate certain operations only when a plate is sensed. For example, when one right sensor is pressed while one left sensor is free, the instrument can perform a washing routine suited for an ELISA plate. When one left sensor 510 is pressed while one right sensor 510 is free, the instrument can perform a washing routine suitable for a cell plate. A fourth option of both sensors 510 pressed can also be used. There can also be more than two switch/sensors 510 along the edge to encode and communicate, a greater amount of information about the plates. Although mechanical switches are shown, other types of switches, including optical and electrical may be employed.

The detection of a plate by physical contact is particularly useful for running a washing process. A washing instrument is designed to run a washing process when a plate is delivered to the instrument by a user or an automated system. When the plate is not properly positioned on the plate stage (or holder), neither contact sensor 510 is pressed, alarming the instrument not to start the washing process. Likewise, when a plate is missing from the instrument by mistake, the washing instrument will not start the process, thereby preventing potentially adverse circumstances. In addition, the differentiation of an ELISA and a cell plate is useful to assure running the right washing process for the type of a plate introduced. A user may mistakenly program the instrument to run a cell assay washing process for an ELISA plate or vice versa. In such case, the washing instrument can stop the process and generate an error message before proceeding to the next step.

A flat slide attached to a plate holder may become bent. Flatness of the slide at the bottom can be extremely important depending on the usage of the plate. Bending of the bottom slide may happen, particularly when the flat slide is made of a flexible or soft material or is thin. Often, the bending or distortion of the bottom slide leads to a poor quality of optical detection because the flatness is important in obtaining high quality of optical data. The tolerance of the flatness may be less stringent, for example 200 um, for an application such as ELISA, where detection is performed by absorbance or epifluorescence method. In an application for cell imaging or microarray imaging, the tolerance is much tighter, for example less than 50 um.

Figure 6:
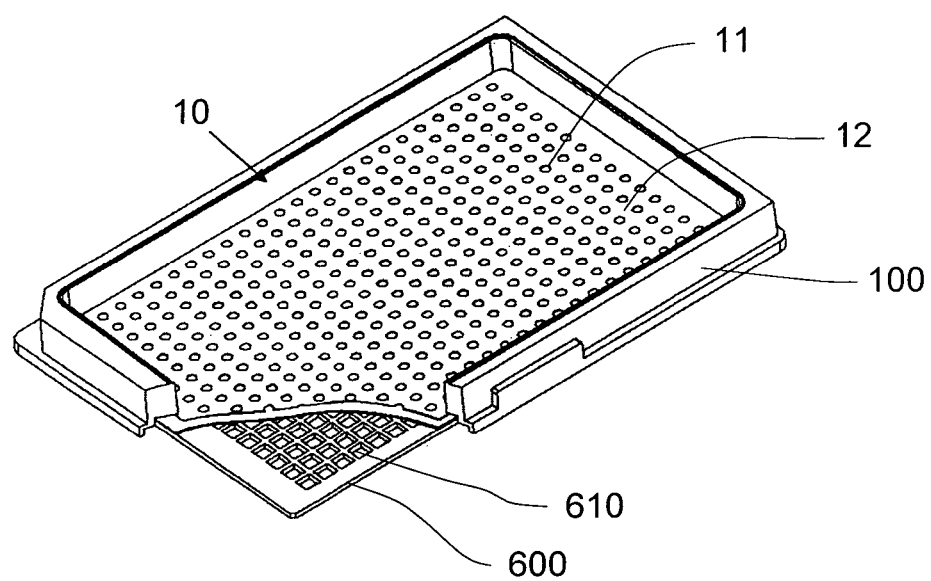
FIG. 6 shows a top perspective view of a plate assembly having a underlying support structure with optical passthroughs, in accordance with an embodiment of the invention.

FIG. 6 shows a plate assembly 10 with a flexible plate 11 in a plate holder 100 supported by a support grid 600. The support grid 600 maintains the flatness of the flexible plate. Using the support grid 600 allows the use of plates that are thinner or made of a more flexible material (including polymeric materials) than would otherwise be practical. Holes 610 in the support grid 600 are arranged to be in-line with hydrophilic elements 12 of the plate 11 thus facilitating optical interrogation thereof, especially in transmission-mode. For example, the grid 600 may be thin enough to allow for optical interrogation by a microscope element from below. By positioning the grid 600 below the plate 11, facile washing of the plate is maintained. The size of the holes can be maximized for easier optical access. Preferably, the grid imparts a flatness of the plate is 200 micrometers or less in deviation from the average elevation over the area of the plate.

Figure 7:
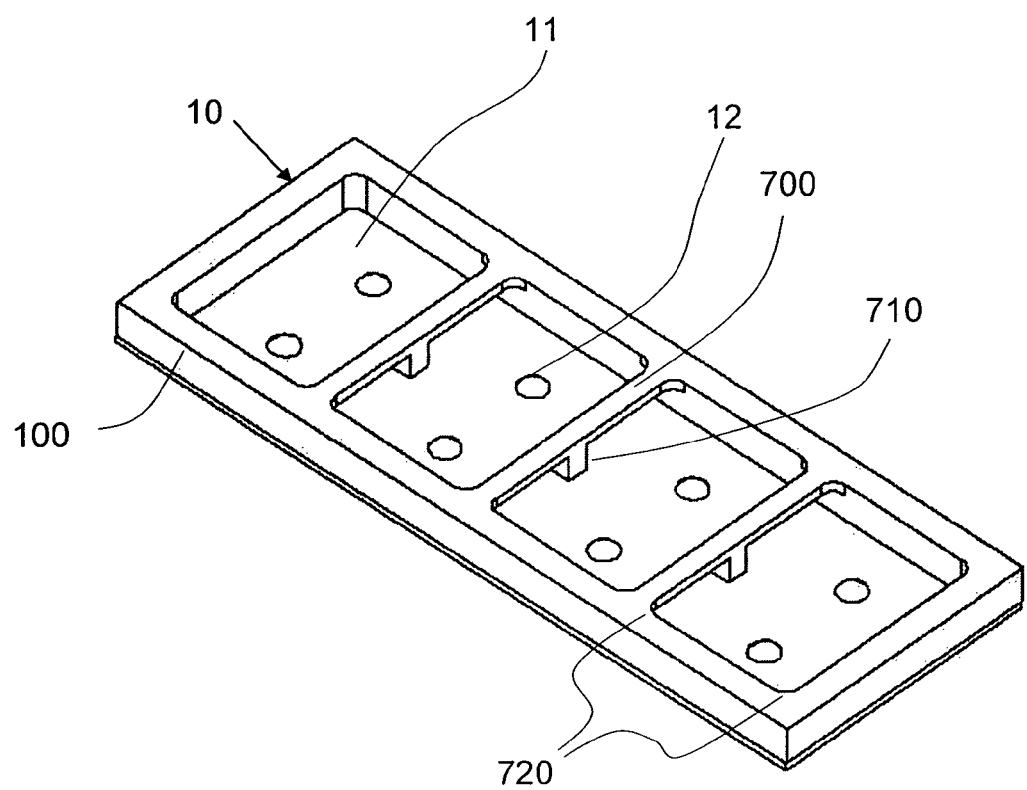
FIG. 7 shows a top perspective view of a plate assembly having a underlying support structure with optical passthroughs and support fingers, in accordance with an embodiment of the invention.

FIG. 7 shows another method for supporting a flexible plate using support pillars 710. The pillars 710 support the positioning of a bottom plate 11 (shown here in a microscope slide aspect ration) but do not interfere with a whole-plate washing of the hydrophilic elements 12. In one example, the plate holder comprises a series of pillars, whose one end contacts a plate 11 and secures the position of the plate 11. In the FIG. 7, the holder 100 contacts the middle of the plate 11 as well as the side of the plate 11. In such manner, the flatness of a plate 11 can be better controlled, particularly when the slide is thin and flexible, for example, a glass slide or plastic slide of thickness 0.17 mm. With the pillars present in the middle of the slide, the surfaces of the pillars may be hydrophobic in order to minimize the wetting of the pillars during exposure to a liquid, in a process such as washing. In addition to the hydrophobic surface property, the pillars can designed to expose round feature instead of edge structure, which is known to help further reduce potential trapping of a liquid or wetting.

The pillars 710 may be disposed on bridges 700, which are disposed between windows 720 that permit optical observation of the elements 12.

In an illustrative embodiment, a bottom slide is a microscope glass slide of 75 mm×25 mm×0.17 mm thickness. For example, the slide holder with pillars has the outer specification of 75 mm×25 mm×5 mm. The holder carries three pillars in the middle of the pocket as shown in FIG. 7. The slide holder is made of, preferably, polypropylene, while the surface, which contacts and bonds to the bottom slide, is treated to become more hydrophilic in order to ensure reasonable bonding of the holder to the slide. The treatment of the surface to become more hydrophilic can be performed by, for example, plasma treatment, which is known to oxidize a polymer surface to become hydrophilic. The size of the pillars is, for example, 1 mm diameter while the bridge holding the pillars is also 1 mm thick with round structure. Preferably, the fingers impart a flatness of the plate is 200 micrometers or less in deviation from the average elevation over the area of the plate. In an alternate embodiment, the fingers may support the under-side of the plate, or the hydrophilic elements may be on the opposing side.

In various embodiments, the holder 100 may have one or any combination of the raised portion 120, the reference corner 125, the sloped portion 130, leveling features 140, and an identification feature 150, a grid 600, pillars 710, or other features mentioned above.

In accordance with an embodiment of the invention, a hydrophobic coating is protected from wetting by a polar liquid (e.g., an aqueous sample). The coating can be created by forming a thin layer of immiscible liquid on top of a solid substrate. In a preferred embodiment, such combination of the solid surface and a thin layer of immiscible liquid satisfies the following conditions: (i) the surface tension of the immiscible liquid is not lower than that of the surface of solid substrate and (ii) the surface tension of the polar liquid is higher than that of the immiscible liquid. For these purposes, a standard solution of phosphate buffered saline may be used as a reference aqueous liquid (137 mM NaCl, 2.7 mM KCl, 10 mM sodium phosphate dibasic, 2 mM potassium phosphate monobasic and a pH of 7.4) to compare surface tensions. In practice, a wide variety of aqueous solutions can be used.

For example, the formation of a thin layer of perfluorocarbon liquid such as perfluorodecane, $CF_3-(CF_2)_9-CF_3$, on a surface of substrate comprising a perfluorocarbon solid such as polytetrafluoroethylene, produces a coating that is resistant to wetting by many types of aqueous solutions. In this case, the surface tension of the immiscible liquid is similar to that of perfluorocarbon solid. In addition, the surface tension of any aqueous solution is higher than that of the immiscible liquid, satisfying the non-wetting condition presented above.

If the vapor pressure of the immiscible liquid is extremely low, then such coating can be produced on a solid substrate and stored for a long time (e.g., more than 2-48 hours or longer). In fact, the coating may last for 6-12 months or more if the package of the solid substrate is adequately sealed to prevent gas exchange. Furthermore, the thin layer of the immiscible liquid is not washed away completely so long as the liquid is not exposed to perfluoro-based liquid. The liquid stays on the solid surface upon exposure to aqueous and organic liquids as the perfluorocarbon-based liquid is immiscible with neither aqueous nor organic liquid.

The thin layer of the immiscible liquid can be applied to any kind of surface including a surface patterned with hydrophobic and hydrophilic coating (e.g., an array of hydrophilic elements on a hydrophobic background). The hydrophobic part can be protected from wetting as far as the system satisfies the relationship of the surface tensions between the surface, immiscible liquid and sample liquid. The hydrophilic part of the surface, however, is expected to interact with the polar liquid if the surface tension of the immiscible is lower than that of the hydrophilic part. If the thin layer of the immiscible liquid is too thick and/or viscous to recede from the hydrophilic part of the surface, the sample liquid may not be able to interact with the hydrophilic part of the surface. The parameters such as the thickness and viscosity of the immiscible liquid may be adjusted in order to allow the sample liquid to interact with the hydrophilic part of the surface. For example, the thickness of the immiscible liquid can be less than 5 mm, or preferably less than 1 mm. The viscosity (kinematic) of the immiscible liquid can be less than 20 cSt, or preferably less than 15 cSt.

The solid hydrophobic background surface may be rough or roughened to prevent outmigration of the immiscible liquid from the hydrophobic regions to the hydrophilic regions. In a preferred embodiment the root mean squared roughness is at least 10 urn or higher, and preferably 50-100 um or greater. The roughness can be a critical parameter because if the hydrophobic area is very smooth, the immiscible liquid may recede from the surface during handling, exposing a dry hydrophobic surface. This leads to the wetting of the dry hydrophobic surface by reagents and solutions in the absence of the immiscible liquid. In an embodiment, the roughness of the hydrophobic background surface, viscosity of the immiscible liquid, and surface tension of the surface and immiscible liquid are chosen so that immiscible liquid remains on the hydrophobic portions of the surface and does not block attachment of aqueous liquids to the hydrophilic elements.

In a specific embodiment, an aqueous solution may be added to one or more array elements after coating with the immiscible liquid and assays may be performed in accordance with the methods of WO2008/063136.

Figure 8:
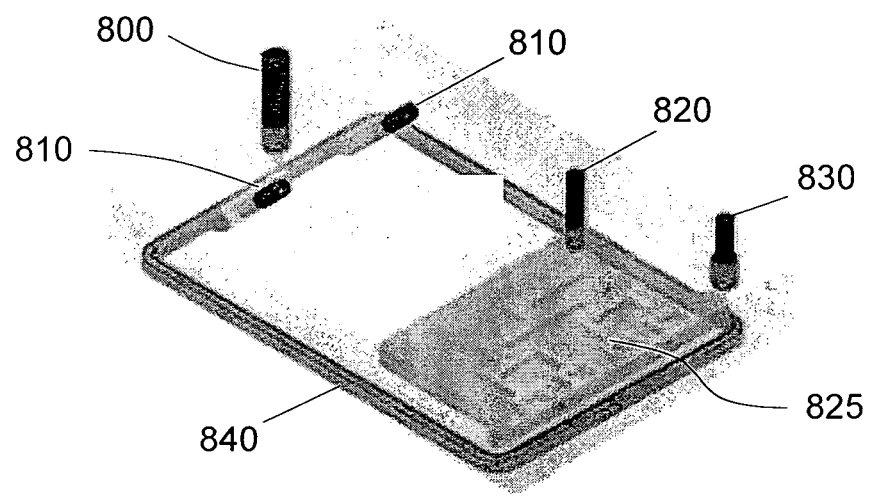
FIG. 8 shows a top perspective view of a cover for a plate assembly, in accordance with an embodiment of the invention.
Figure 9:
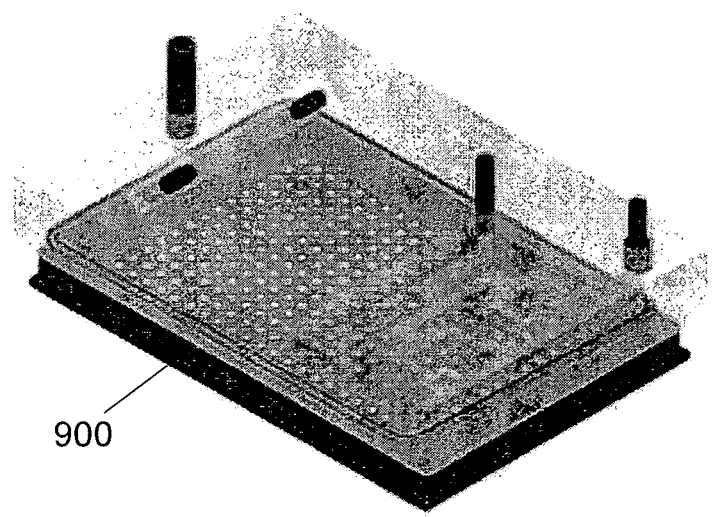
FIG. 9 shows a top perspective view of a covered plate assembly, in accordance with an embodiment of the invention.
Figure 10:
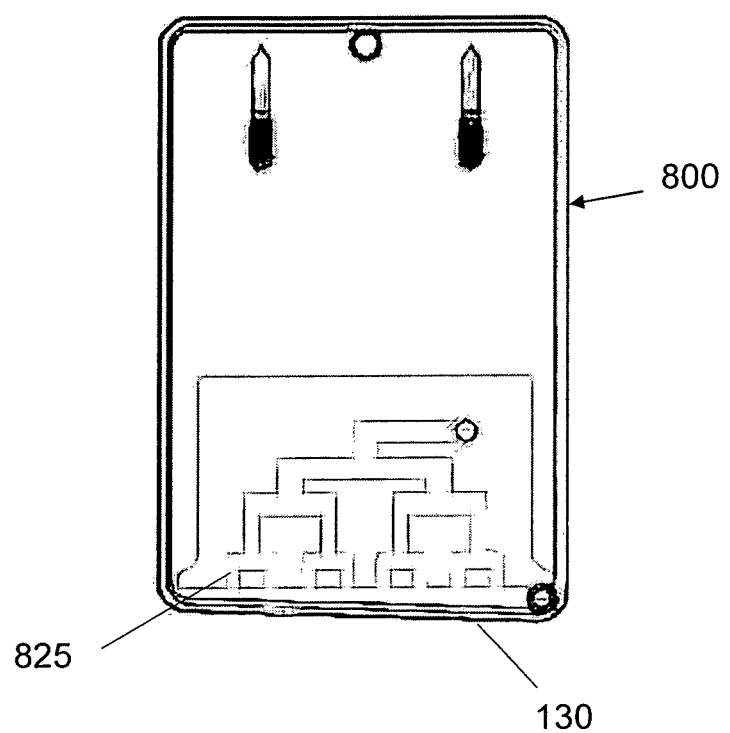
FIG. 10 shows a plan view of a covered plate assembly, in accordance with an embodiment of the invention.

FIGS. 8-11 show illustrative embodiments of a cover 800 that is adapted to fit sealingly on plate holder 100. FIG. 8 shows the cover 800 and FIG. 9 shows the cover 800 in an assembly 900 with a plate holder 100 and plate 11. The cover 800 includes several features that may be used individually, or combined in various combinations. An elastomeric gasket 840 is positioned to seal against a raised ridge 120 of the holder 100. As described in herein and in WO2008/063136, hydrophobic immiscible oil may be added to coat the array. The oil may be injected via one or more inlets 810. Angular cutout 811 can be included as an optional design feature. An air vent 800 may be used to prevent unwanted backpressure. The angle of the oil inlet is directed away from the center of the plate so as not to stream oil directly at the hydrophilic elements, which are typically centrally placed. The angle may be chosen to impact the wall 110 of the plate holder 100. In this way, droplets of polar liquid adhered to the elements will not be displaced. The introduction of oil can be made gentler by using multiple oil inlets 800. In a related embodiment, oil can be introduced using a branched structure as described below in connection with a wash buffer.

A wash liquid input system is also provided. Wash liquid (e.g. a buffered aqueous solution) may be introduced via a wash-buffer inlet 820. The wash buffer travels through a branched channel structure 825, which splits the flow of the buffer and introduces the buffer to the chamber formed between the plate 11 and the cover 840. In practice, the assembly 900 may be tilted from the horizontal so that wash buffer is introduced so as to fill the chamber from the bottom up, thereby effecting an even and gentle filling of the chamber. For example, the liquid can be split into 8 streams. Each of the exit channels may, for example, have a width of 1-5 mm, preferably 2-3 mm, with a height of 0.1-0.2 mm, preferably 0.2-1.5 mm, although other configurations are possible. The assembly 900 can be then tilted back to horizontal for shaking, prior to draining.

Figure 11:
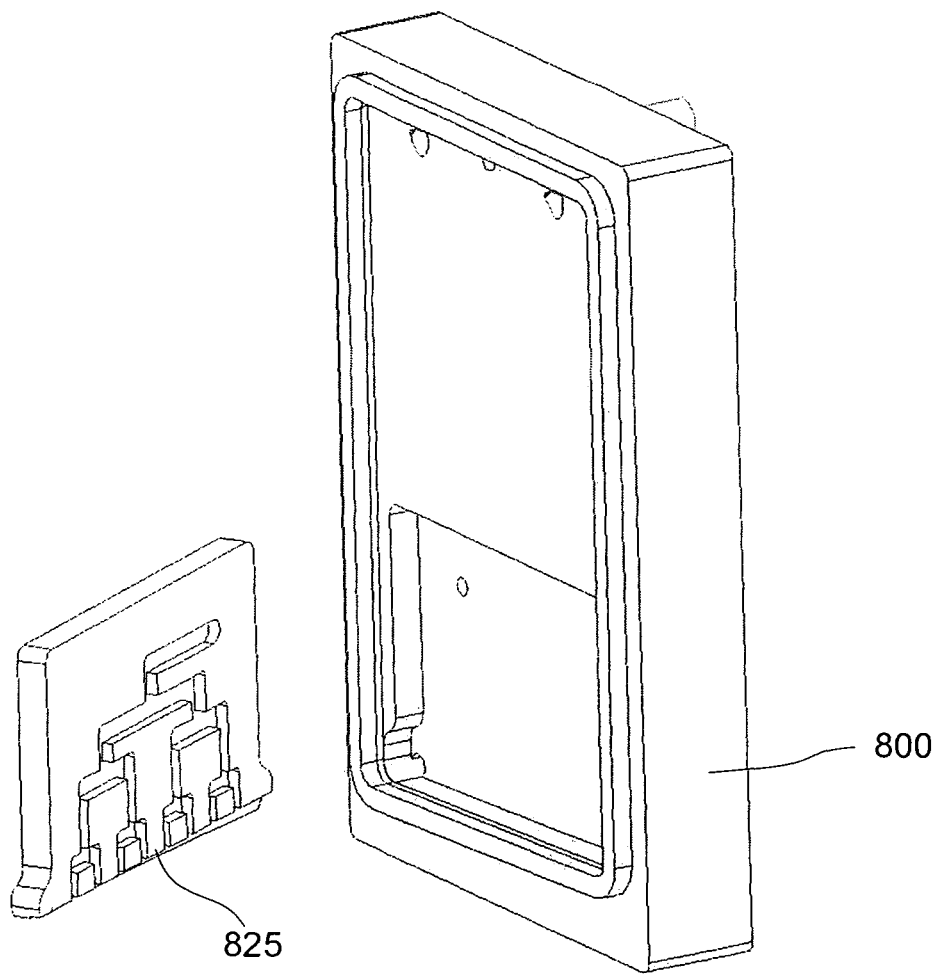
FIG. 11 shows an exploded view of a cover for a plate assembly, in accordance with an embodiment of the invention.

FIG. 11 shows a plan view of an embodiment of the assembly 900, further including a sloped portion 130. FIG. 11 shows how the branched channel structure 825 and the rest of the cover 800 may be assembled from 2 pieces.

Figure 12:
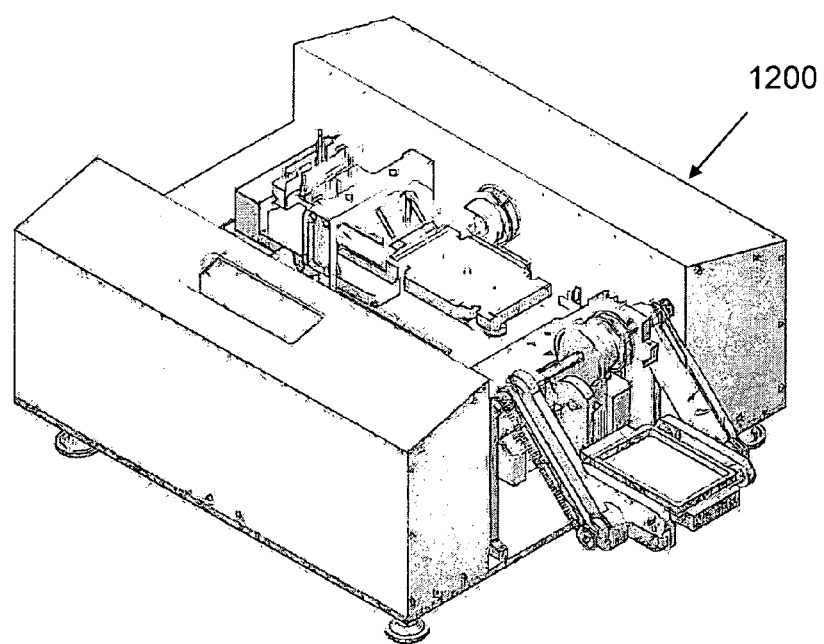
FIG. 12 shows a top perspective view of an instrument for automated plate washing, in accordance with an embodiment of the invention.

FIG. 12 shows a top perspective view of a plate washing instrument 1200, in accordance with an embodiment of the invention. The plate washing instrument is designed to wash a plate 11. The washing instrument 1200 can include a mechanism for draining a hydrophobic liquid from a plate assembly 900, a mechanism for filling the assembly with an aqueous wash liquid, a mechanism for shaking the assembly in the presence of the aqueous wash liquid; a mechanism for tilting and thereby draining the wash liquid from the assembly, and a spill sensor placed under the assembly to trigger an alarm condition if the spill sensor is contacted by wash liquid. In addition, the washing instrument 1200 a reader adapted to read information from the assembly and to use the information to authenticate the source of the plate, to control the plate washing process by setting one or more parameters such as a first type of wash buffer, a first volume of wash buffer, a first shaking duration, a first shaking speed, a first rest duration before draining, a first draining duration, a first draining angle a second wash buffer, a second wash volume, a second shaking duration, a second shaking speed, a second rest duration before draining, a second draining duration, and a second draining angle, to confirm that the plate is mounted on the machine in a safe or desired location, to identify the number or arrangement of hydrophilic features on the plate, to record the date of production of the plate, to record the date of expiry of the plate, and/or to record the number of times the plate has been washed, and optionally, a writing device for use with an writable identification feature such as an RFID device the writing device operable to store information on the identification feature such as an update to the number of times the plate has been washed.

Figure 13:
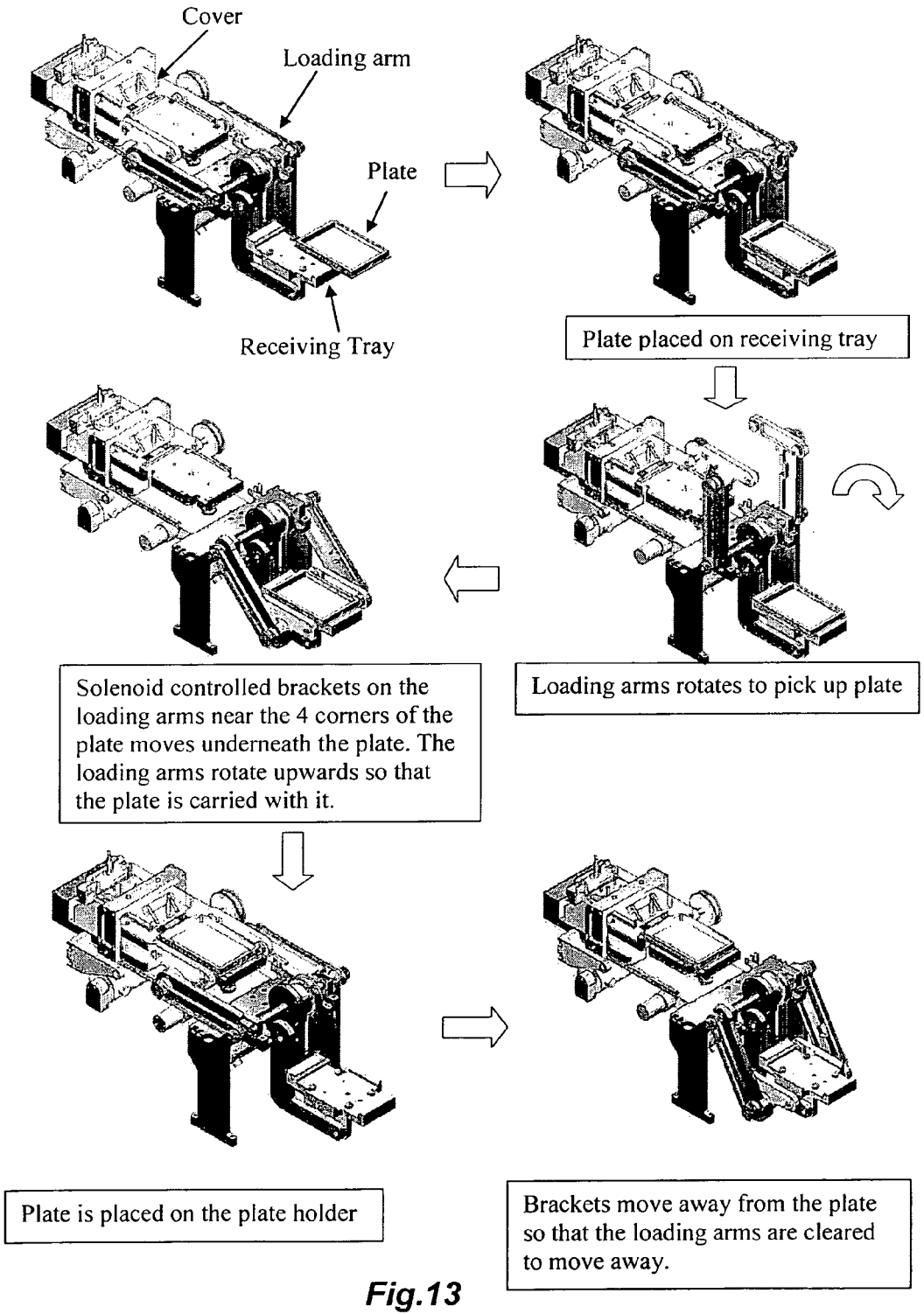
FIG. 13 shows a sequence of operations for loading a plate assembly onto the washing instrument of FIG. 12, in accordance with an embodiment of the invention.
Figure 14:
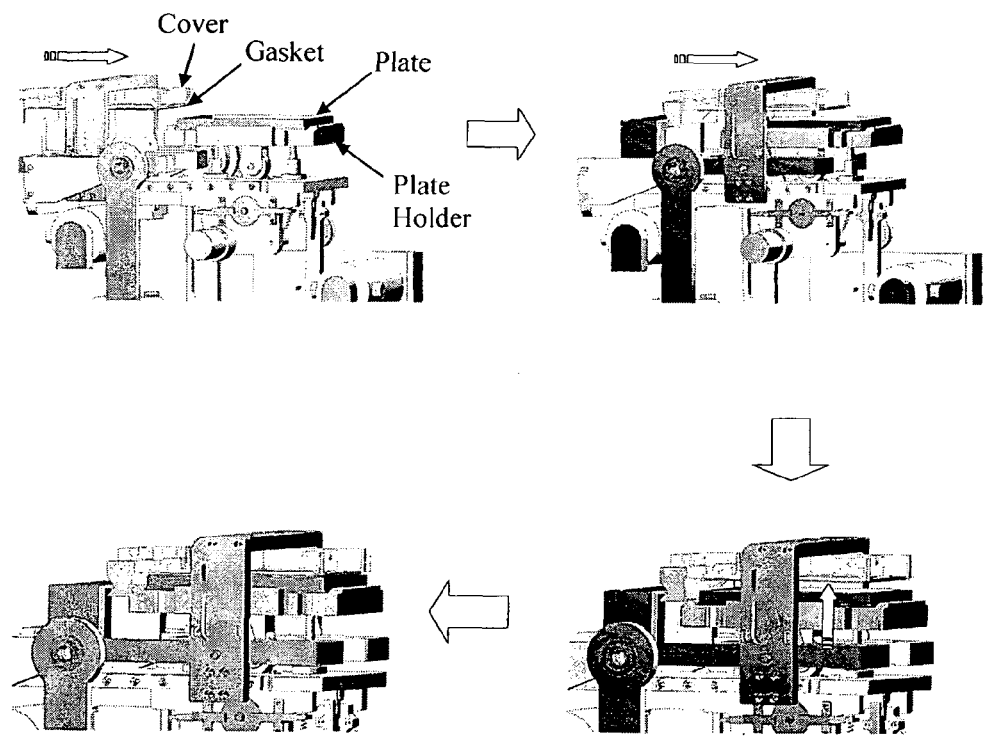
FIG. 14 shows a sequence of operations for covering a plate assembly using the washing instrument of FIG. 12, in accordance with an embodiment of the invention.
Figure 15:
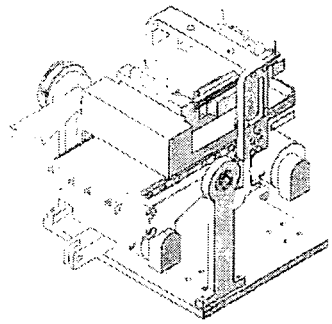
FIG. 15 shows a sequence of operations for tilting the covered plate assembly of FIG. 14 in order to perform fluid exchange operations, in accordance with an embodiment of the invention.
Figure 15:
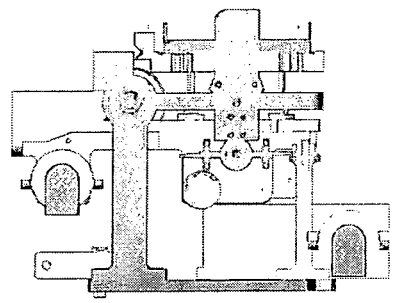
Figure 15:
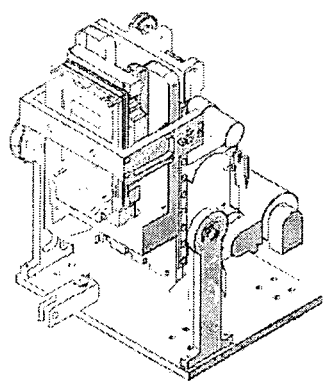
Figure 15:
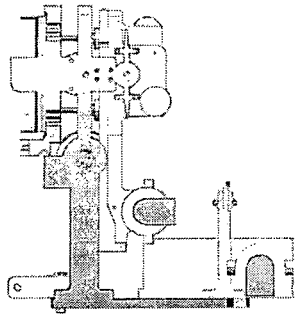
Figure 15:
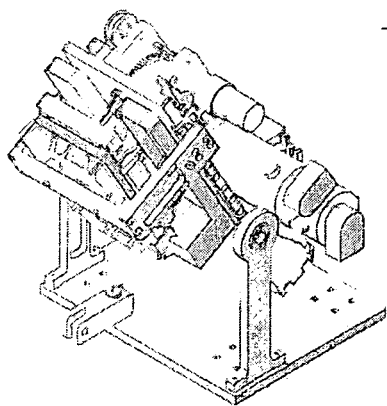
Figure 15:
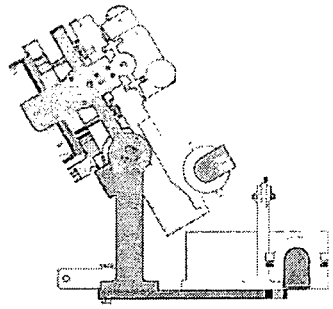

FIG. 13 shows a sequence of operations of instrument 1200 in loading a plate/holder assembly 10. FIG. 14 shows a sequence of machine operations in which a cover 800 is pressed against a plate/holder assembly 10, to form a covered assembly 900.

FIG. 14 shows a sequence of machine operations in which the covered assembly 900 is tilted at various angles for addition and removal of immiscible oil and wash buffer, which may be effected automatically using an automated fluid exchange system. In the method of WO2008/063136, the wash buffer was drained at 120 degrees from horizontal. This angle gives effective draining to minimize residual volume. In an embodiment of the present invention, however, it is realized that for some assay operations, it may be desirable to retain more than a minimal amount of polar liquid on the hydrophilic elements after draining. Accordingly, the present invention features a method for controlling a residual volume of an aqueous solution bathing an array comprising a plurality of hydrophilic elements on a hydrophobic background. The method includes adding an aqueous liquid to the array so as to contact the hydrophilic elements and tilting the array to a selected angle from a horizontal reference plane, wherein the angle is less than 120 degrees and preferably between 5 degrees and 115 degrees, (more preferably between 15 and 90 degrees), and allowing the aqueous liquid to drain while leaving a residual volume adhered to the elements. A desired residual volume may be selected and a corresponding angle selected so as to leave behind the desired residual volume. This may be accomplished by performing calibration experiments to create a lookup table correlating angle to volume.

Figure 16:
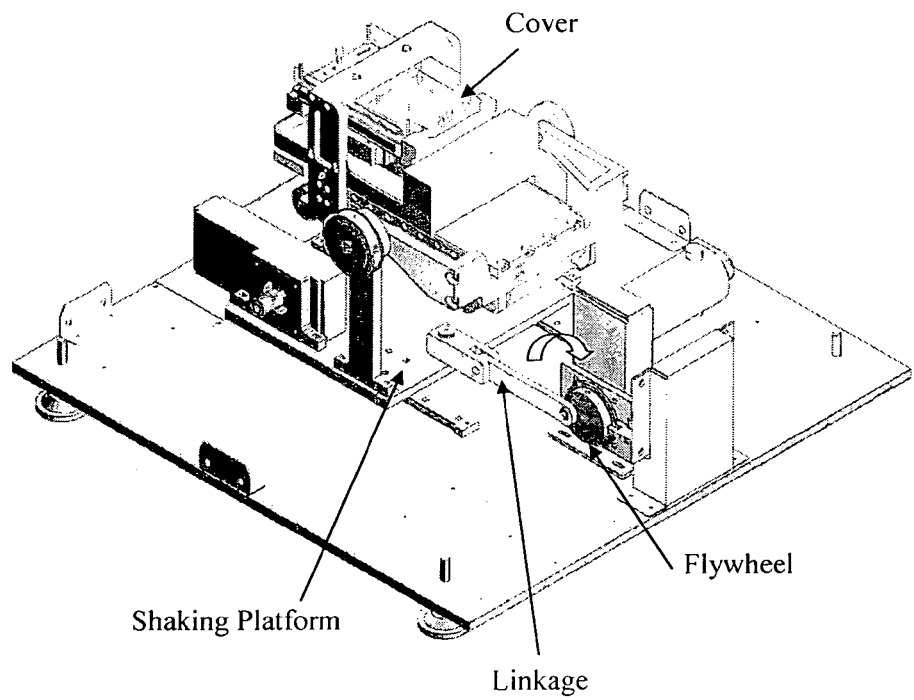
FIG. 16 shows a sequence of operations for shaking the covered plate assembly of FIG. 14, in accordance with an embodiment of the invention.
Figure 16:
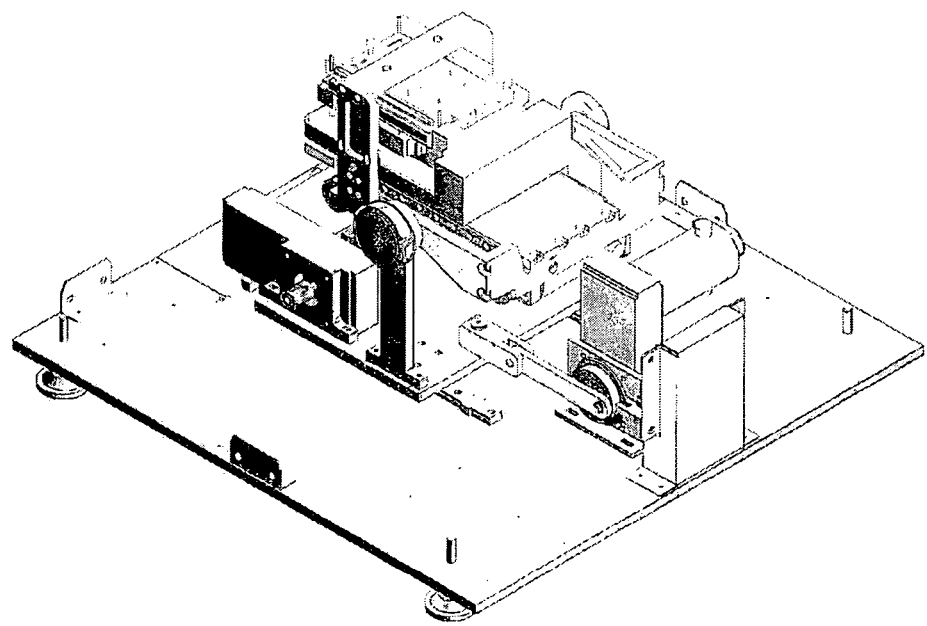

The correlations may also be described by a computational fit to the data (i.e., parameterizing a model equation). For example, using 2 mm diameter hydrophilic regions with adhered PBS buffer, the residual volume after draining approximately correlates to the draining angle as follows:

30 degrees: 0.6-0.8 microliter retained per element
60 degrees: 0.4-0.6 microliter retained per element
90 degrees: 0.2-0.3 microliter retained per element FIG. 16 shows a sequence of operations for shaking the covered assembly 900 in order to wash the hydrophilic elements of the plate 11. A rotating flywheel attached to a linkage imparts an oscillating motion to a shaking platform. The motion causes the wash buffer to splash from side to side, thus creating a washing action.

Figure 17:
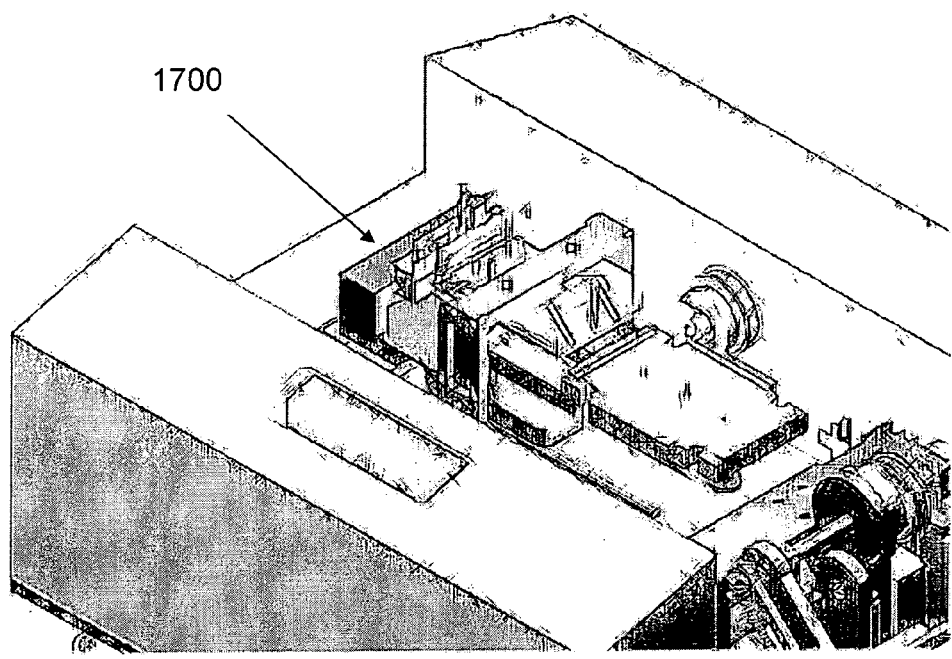
FIG. 17 shows a top perspective view of the instrument of FIG. 12 in which there is a plate holder with RFID antenna and a spill tray.

FIG. 17 shows a safety feature of instrument 1200 in accordance with an embodiment of the invention. A spill tray 1700 includes a liquid sensor (e.g. the one shown in FIG. 18). The spill tray 1700 serves two major safety roles in the event of leakage. First, the spill tray 1700 contains majority of the spilled liquid and prevents the liquid leak into the inside of electromechanical section of the instrument.

Figure 18:
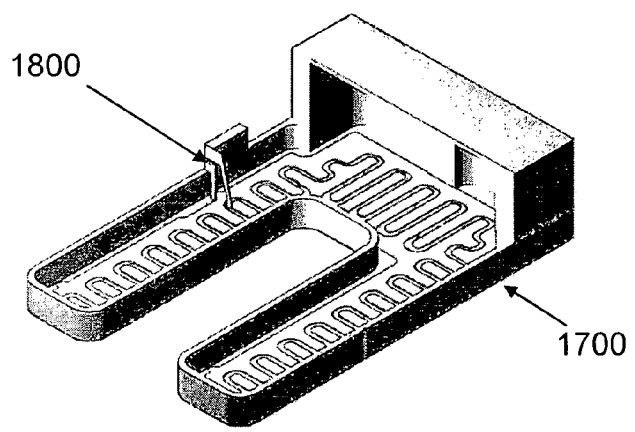
FIG. 18 shows a close-up top perspective view of the spill tray of FIG. 17.
Figure 19:
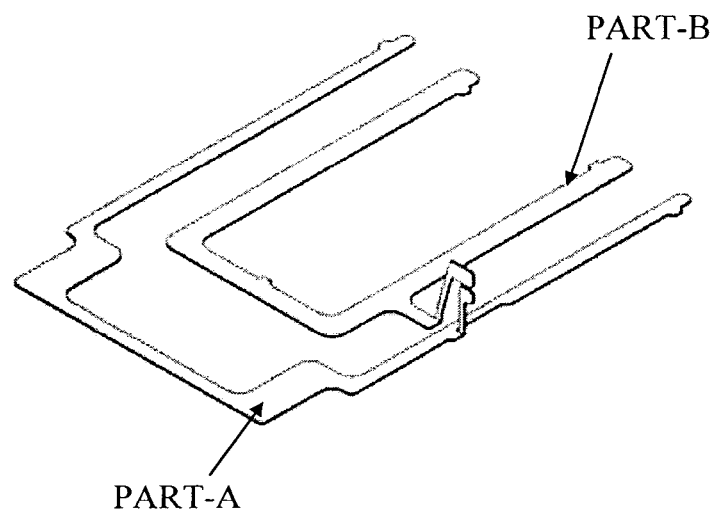
FIG. 19 schematically shows a liquid sensor of the spill tray of FIG. 18.

Second, the tray carries two conducting pieces separated by in the range of 1 mm-10 cm, preferably 0.5 cm-3 cm by average. In case of any spillage, a circuit is completed between the two separated pieces, thereby triggering an alarm condition, for example, stopping the ongoing machine operation for manual intervention and repair. FIG. 18 shows an example of a tray 1700 and two separate pieces of electrodes integrated into the tray forming the liquid sensor 1800. The threshold volume of aqueous solution required in order to trigger the alarm may be adjusted by selecting a distance of the electrode; a larger distance will be sensitive only to larger liquid drops. FIG. 19 shows an embodiment of the liquid sensor 1800.

Figure 20:
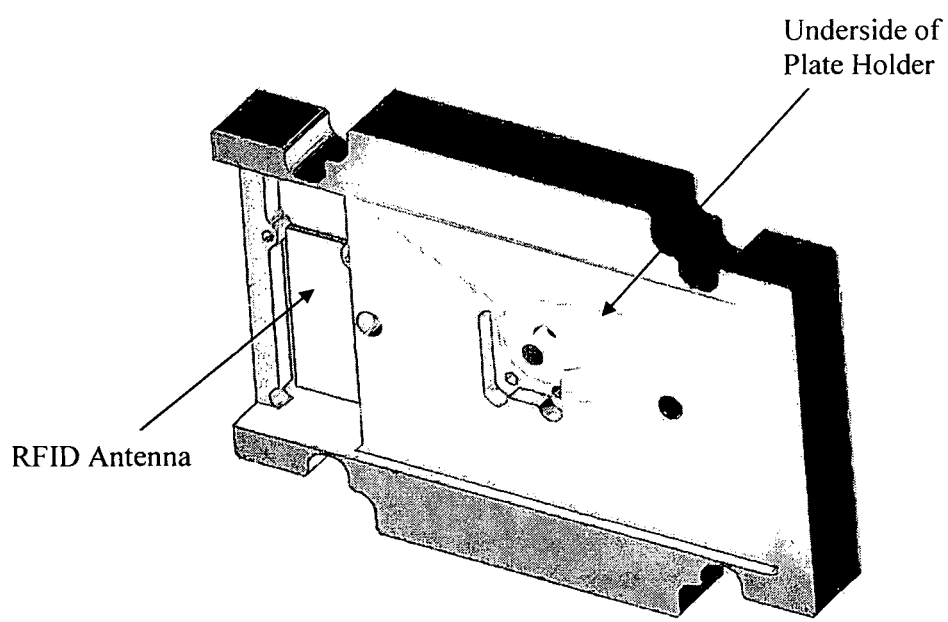
FIG. 20 shows a perspective view of the underside of a plate holder of the instrument of FIG. 12 having an RFID reader.

FIG. 20 shows the underside of a plate holder of an instrument 1200 in accordance with an embodiment of the invention. The plate holder is made of a non-conducting material, and has a small pocket to allow a RFID reader/writer antenna to be mounted. The RFID reader/writer antenna is printed on a Printed Circuit Board (PCB). The antenna is connected to a remotely placed RFID reader/writer module by electrical cable. The RFID module, when activated, will detect the presence of a plate with an RFID tag. The detection will act as a safety feature to confirm the plate presence before activating the washing cycle, and also for the purpose of information gathering such as the type of plate or other information described above.

In alternative embodiments, the disclosed methods for instrument control and assay may be implemented as a computer program product for use with a computer system. For example, a control system for an embodiment of the above described washing instrument may be sold as a computer program product for use with an existing washing instrument. Such implementations may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems.

Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although the above discussion discloses various exemplary embodiments of the invention, it should be apparent that those skilled in the art can make various modifications that will achieve some of the advantages of the invention without departing from the true scope of the invention.

The invention claimed is:

1. A combination of a liquid handling plate and a holder for holding the liquid handling plate, the combination comprising:
   a generally rectangular frame sized to hold the plate and having a circumferential side wall; and
   the plate comprising a device for holding an array of aqueous liquid droplets, the device comprising a pattern of hydrophilic liquid-capturing elements on a hydrophobic background, the hydrophobic background coated by a layer of hydrophobic liquid that imparts additional non-wetting characteristics to the hydrophobic background when challenged with an aqueous liquid, wherein the hydrophobic liquid is immiscible with the aqueous liquid and wherein the surface tension of the hydrophobic liquid is equal to or greater than the surface tension of the hydrophobic background and the surface tension of the hydrophobic liquid is lower than that of the aqueous liquid, wherein the layer of hydrophobic liquid is less than 5 mm thick,
   wherein at least one portion of the side wall of the frame has a sloping feature having a slope such that when the plate is mounted in the frame to form a mounted structure and a liquid is held in the mounted structure so as to contact the frame in a draining position, gravity will cause the liquid to be drawn downward along the slope.

2. The combination of claim 1, further comprising an identification feature suitable for communication with an automated instrument for washing the mounted structure, the identification feature usable to authenticate the source of the plate,
   to control the plate washing process by setting one or more parameters such as a first type of wash buffer, a first volume of wash buffer, a first shaking duration, a first shaking speed, a first rest duration before draining, a first draining duration, a first draining angle a second wash buffer, a second wash volume, a second shaking duration, a second shaking speed, a second rest duration before draining, a second draining duration, and a second draining angle,
   to confirm that the plate is mounted on the machine in a safe or desired location, to identify the number or arrangement of hydrophilic features on the plate, and/or to record the date of production of the plate, the date of expiry of the plate, or the number of times the plate has been washed.

3. The combination of claim 1, further comprising a plurality of feet sized to elevate the plate by a fixed amount to thereby create a gap which enhances the parallel positioning of the plate relative to the holder when a sealant such as an adhesive or elastomer is positioned in the gap.

4. The combination of claim 1, further comprising a raised portion mounted atop the side wall for sealingly contacting a cover when pressed against a gasket, the raised portion positioned near the inside edge of the side wall.

5. The combination of claim 1, wherein the plate is positioned with a flatness of less than 200 micrometers over the area of the plate.

6. The combination of claim 1, further comprising at least one cutout positioned on the holder to mechanically signal information to an array of switches on a receiving platform of a corresponding plate washing instrument.

7. A liquid handling plate, the plate comprising:
an array of hydrophilic regions in a hydrophobic background, the hydrophilic regions arranged with an industry standard microplate spacing;
an array holder for mounting the array; and
an identification feature suitable for communication with an automated instrument for washing the mounted structure to perform an assay,
wherein the plate comprises a device for holding an array of aqueous liquid droplets, the device comprising a pattern of hydrophilic liquid-capturing elements on a hydrophobic background, the hydrophobic background coated by a layer of hydrophobic liquid that imparts additional nonwetting characteristics to the hydrophobic background when challenged with an aqueous liquid, wherein the hydrophobic liquid is immiscible with the aqueous liquid and wherein the surface tension of the hydrophobic liquid is equal to or greater than the surface tension of the hydrophobic background and the surface tension of the hydrophobic liquid is lower than that of the aqueous liquid, wherein the layer of hydrophobic liquid is less than 5 mm thick.

8. The plate of claim 7, wherein the identification feature carries information usable by a plate washing machine.

9. The plate of claim 7, wherein the array holder comprises sidewalls, the plate further comprising a raised portion atop the side wall for sealingly contacting a cover when pressed against a gasket, the raised portion positioned near the inside edge of the side wall.

10. The plate of claim 7, further comprising a support grid adapted to support a substrate in a generally planar position and having openings aligned with the hydrophilic regions so as to permit optical interrogation thereof.

11. A system comprising the plate of claim 7, wherein the identification feature comprises a cutout positioned for actuating an array of switches on a receiving platform of a plate washing machine.

12. A combination of a fluidic plate and a fluid-exchange cover for sealingly covering the fluidic plate, the cover including a fluidic channel system, the fluidic channel system comprising one or both of:
an oil inlet arranged so that when the cover is held sealingly against a fluidic plate having a wall, fluid injected into the inlet is directed against the wall in a manner that does not disrupt liquid adhered to hydrophilic regions of the plate; and
a washing liquid inlet in communication with a branched channel structure that divides the flow of washing liquid injected into the channel so as to lessen a potential impact of the washing liquid against the hydrophilic elements,
wherein the combination comprises the plate, and the plate comprises a device for holding an array of aqueous liquid droplets, the device comprising a pattern of hydrophilic liquid-capturing elements on a hydrophobic background, the hydrophobic background coated by a layer of hydrophobic liquid that imparts additional nonwetting characteristics to the hydrophobic background when challenged with an aqueous liquid, wherein the hydrophobic liquid is immiscible with the aqueous liquid and wherein the surface tension of the hydrophobic liquid is equal to or greater than the surface tension of the hydrophobic background and the surface tension of the hydrophobic liquid is lower than that of the aqueous liquid, wherein the layer of hydrophobic liquid is less than 5 mm thick.

13. A method for controlling a residual volume of an aqueous solution bathing an array comprising a plurality of hydrophilic elements on a hydrophobic background, the method comprising:
adding an aqueous liquid so as to contact the hydrophilic elements;
tilting the array to a selected angle from a horizontal reference plane, wherein the angle is less than 120 degrees; and
allowing the aqueous liquid to drain while leaving a residual volume adhered to the elements,
wherein the array comprises a device for holding an array of aqueous liquid droplets, the device comprising a pattern of hydrophilic liquid-capturing elements on a hydrophobic background, the hydrophobic background coated by a layer of hydrophobic liquid that imparts additional nonwetting characteristics to the hydrophobic background when challenged with an aqueous liquid, wherein the hydrophobic liquid is immiscible with the aqueous liquid and wherein the surface tension of the hydrophobic liquid is equal to or greater than the surface tension of the hydrophobic background and the surface tension of the hydrophobic liquid is lower than that of the aqueous liquid, wherein the layer of hydrophobic liquid is less than 5 mm thick.

14. The method of claim 13, further comprising selecting a desired residual volume and selecting a corresponding angle so as to leave behind the desired residual volume.

15. A device for holding an array of aqueous liquid droplets, the device comprising a pattern of hydrophilic liquid-capturing elements on a hydrophobic background, the hydrophobic background coated by a layer of hydrophobic liquid that imparts additional nonwetting characteristics to the hydrophobic background when challenged with an aqueous liquid, wherein the hydrophilic liquid-capturing elements and the hydrophobic background are formed on a flat continuous surface, the hydrophilic liquid-capturing elements are exposed from the layer of hydrophobic liquid to receive the aqueous liquid droplets, the hydrophobic liquid is immiscible with the aqueous liquid, and wherein the surface tension of the hydrophobic liquid is equal to or greater than the surface tension of the hydrophobic background and the surface tension of the hydrophobic liquid is lower than that of the aqueous liquid.

16. The device of claim 15, wherein the flatness of the flat surface is 200 micrometers or less.

17. The device of claim 15, wherein the hydrophobic liquid has a kinematic viscosity of less than 15 cSt.

18. A device for holding an array of aqueous liquid droplets, the device comprising a pattern of hydrophilic liquid-capturing elements on a hydrophobic background, the hydrophobic background coated by a layer of hydrophobic liquid that imparts additional nonwetting characteristics to the hydrophobic background when challenged with an aqueous liquid, wherein the hydrophobic liquid is immiscible with the aqueous liquid and wherein the surface tension of the hydrophobic liquid is equal to or greater than the surface tension of the hydrophobic background and the surface tension of the hydrophobic liquid is lower than that of the aqueous liquid, wherein the hydrophobic liquid has a kinematic viscosity of less than 20 cSt, wherein the layer of hydrophobic liquid is less than 5 mm thick.

19. The device of claim 15, wherein the hydrophobic liquid comprises a perfluorocarbon, the perfluorocarbon having a vapor pressure low enough to allow use of the device without exposing the hydrophobic background for 2 or more hours.

20. The device of claim 15, packaged to prevent gas exchange, so as to maintain the immiscible liquid for 6-12 months or more.

21. The device of claim 15, further comprising a roughened hydrophobic background, the roughness of the hydrophobic background characterized by a root mean squared roughness of 50-100 micrometers or greater.

22. A method for protecting a hydrophobic background from wetting by a liquid introduced to an array of hydrophilic elements adjacent to the hydrophobic background, the method comprising:
selectively coating, prior to challenging with an aqueous liquid, the hydrophobic background with a layer of hydrophobic liquid that imparts additional nonwetting characteristics to the hydrophobic background when challenged with an aqueous liquid, while the hydrophilic elements are exposed from the layer of hydrophobic liquid to receive the aqueous liquid, so that the hydrophobic liquid remains on the hydrophobic background and does not block the array of hydrophilic elements,
wherein the hydrophobic liquid is immiscible with the aqueous liquid and wherein the surface tension of the hydrophobic liquid is equal to or greater than the surface tension of the hydrophobic background and the surface tension of the hydrophobic liquid is lower than that of the aqueous liquid.

23. The method of claim 22, wherein the aqueous liquid is phosphate buffered saline.

24. The method of claim 22, wherein the hydrophobic liquid has a kinematic viscosity of less than 20 cSt.

25. The method of claim 22, wherein the hydrophobic liquid comprises a perfluorocarbon, the perfluorocarbon having a vapor pressure low enough to allow use of the device without exposing the hydrophobic background for 2 or more hours.

26. The method of claim 22, further comprising using a roughened hydrophobic background, the roughness of the hydrophobic background sufficient to prevent outmigration of the hydrophobic liquid and characterized by a root mean squared roughness of 50-100 micrometers or greater.

27. The method of claim 22, further comprising performing an assay, the assay comprising adding an aqueous liquid sample or reagent to the array while it is coated with the hydrophobic liquid.

28. The method of claim 26, wherein the roughness of the hydrophobic background, viscosity of the hydrophobic liquid, surface tension of the background, and surface tension of the hydrophobic liquid are chosen so that the hydrophobic liquid remains on the hydrophobic portions of the surface and does not block attachment of the aqueous liquids to the hydrophilic elements.

29. A combination of a deformable transparent microfluidic substrate and a frame for holding the deformable transparent microfluidic substrate, the frame comprising a plurality of support pillars positioned to hold a substrate in a flat configuration, the pillars separated by cutout portions,
wherein the combination comprises the substrate, and the substrate comprises a device for holding an array of aqueous liquid droplets, the device comprising a pattern of hydrophilic liquid-capturing elements on a hydrophobic background, the hydrophobic background coated by a layer of hydrophobic liquid that imparts additional nonwetting characteristics to the hydrophobic background when challenged with an aqueous liquid, wherein the hydrophobic liquid is immiscible with the aqueous liquid and wherein the surface tension of the hydrophobic liquid is equal to or greater than the surface tension of the hydrophobic background and the surface tension of the hydrophobic liquid is lower than that of the aqueous liquid, wherein the layer of hydrophobic liquid is less than 5 mm thick.

30. The combination according to claim 29, wherein the pillars are rounded and/or hydrophobic to reduce the potential for wetting of the pillars.

31. An assay array comprising: a deformable microfluidic substrate in a generally planar configuration, a generally rectangular border extending normal to the plane of the substrate, and a supporting grid below the substrate, the substrate having an array of hydrophilic elements in a hydrophobic background and the grid having openings aligned with the hydrophilic elements to permit optical transmission through both the grid and the hydrophilic elements, wherein the array comprises a device for holding an array of aqueous liquid droplets, the device comprising a pattern of hydrophilic liquid-capturing elements on a hydrophobic background, the hydrophobic background coated by a layer of hydrophobic liquid that imparts additional nonwetting characteristics to the hydrophobic background when challenged with an aqueous liquid, wherein the hydrophobic liquid is immiscible with the aqueous liquid and wherein the surface tension of the hydrophobic liquid is equal to or greater than the surface tension of the hydrophobic background and the surface tension of the hydrophobic liquid is lower than that of the aqueous liquid, wherein the layer of hydrophobic liquid is less than 5 mm thick.

32. A device for holding an array of aqueous liquid droplets, the device comprising a pattern of hydrophilic liquid-capturing elements on a hydrophobic background, the hydrophobic background coated by a layer of hydrophobic liquid that imparts additional nonwetting characteristics to the hydrophobic background when challenged with an aqueous liquid, wherein the hydrophobic liquid is immiscible with the aqueous liquid and wherein the surface tension of the hydrophobic liquid is equal to or greater than the surface tension of the hydrophobic background and the surface tension of the hydrophobic liquid is lower than that of the aqueous liquid, wherein the layer of hydrophobic liquid is less than 5 mm thick.

* * * * *